(12) United States Patent
Strom et al.

(10) Patent No.: US 6,281,193 B1
(45) Date of Patent: Aug. 28, 2001

(54) COMPOUNDS THAT INHIBIT THE BINDING OF RAF-1 OR 14-3-3 PROTEINS TO THE BETA CHAIN OF IL-2 RECEPTOR, AND PHARMACEUTICAL COMPOSITIONS CONTAINING SAME

(75) Inventors: Terry Strom, Brookline, MA (US); Wlodzimierz Maslinski, Warsaw (PL)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/194,145
(22) PCT Filed: May 22, 1997
(86) PCT No.: PCT/US97/08542
   § 371 Date: Mar. 8, 1999
   § 102(e) Date: Mar. 8, 1999
(87) PCT Pub. No.: WO97/44058
   PCT Pub. Date: Nov. 27, 1997

Related U.S. Application Data
(60) Provisional application No. 60/018,183, filed on May 23, 1996, now abandoned.

(51) Int. Cl.[7] ............ A61K 38/20; A61K 45/00; C07K 14/715
(52) U.S. Cl. .......... 514/12; 424/278.1; 424/810; 530/324
(58) Field of Search .................. 530/300, 350, 530/387.9, 388.1, 388.22, 389.1, 324, 402; 424/139.1, 143.1, 185.1, 278.1, 810; 514/1, 2, 8, 12

(56) References Cited

PUBLICATIONS

Hatakeyama et al. Science 244:551–556, 1989.*
Pang et al Blood 80:724–732, 1992.*
Kawamoto, et al, Cytotechnology 17:103–108, 1995.*
Skoulakis et al. Neuron 17 (5):931–44, 1996.*
Janeway et al. Immunobiology: The Immune System in Health and Disease, 3rd Edition, pp. 10:22 and 12:19, 1997.*
Ngo et al., The Protein Folding Problem and Tertiary Structure Prediction, Merz et al (ed) Birkhauser, Boston MA pp. 433 and 492–495, 1994.*
Kolch et al., Oncogene 5:713–720, 1990.*
Liblau et al., Immunology Today, 18:599–604, 1997.*
Paul, William, Fundamental Immunology, 4th Edition, Lippincott–Raven, Philadelphia, PA, 1999.*

* cited by examiner

*Primary Examiner*—David Saunders
*Assistant Examiner*—Amy DeCloux
(74) *Attorney, Agent, or Firm*—Browdy and Neimark

(57) ABSTRACT

The invention relates to compounds, such as proteins, peptides and organic compounds, capable of blocking or inhibiting the binding interaction of Raf-1 or 14-3-3 proteins to the $\beta$ chain of IL-2, and pharmaceutical compositions containing such compounds. In vitro assays for isolating, identifying and characterizing such compound capable of inhibiting interaction of Raf-1 or 14-3-3 proteins to IL-2$\beta$ are also provided.

2 Claims, 11 Drawing Sheets

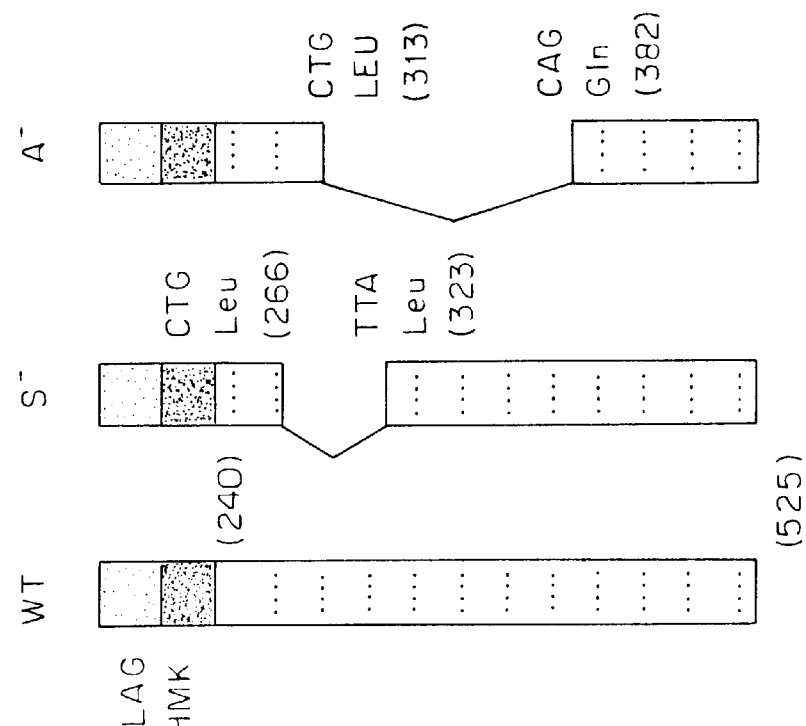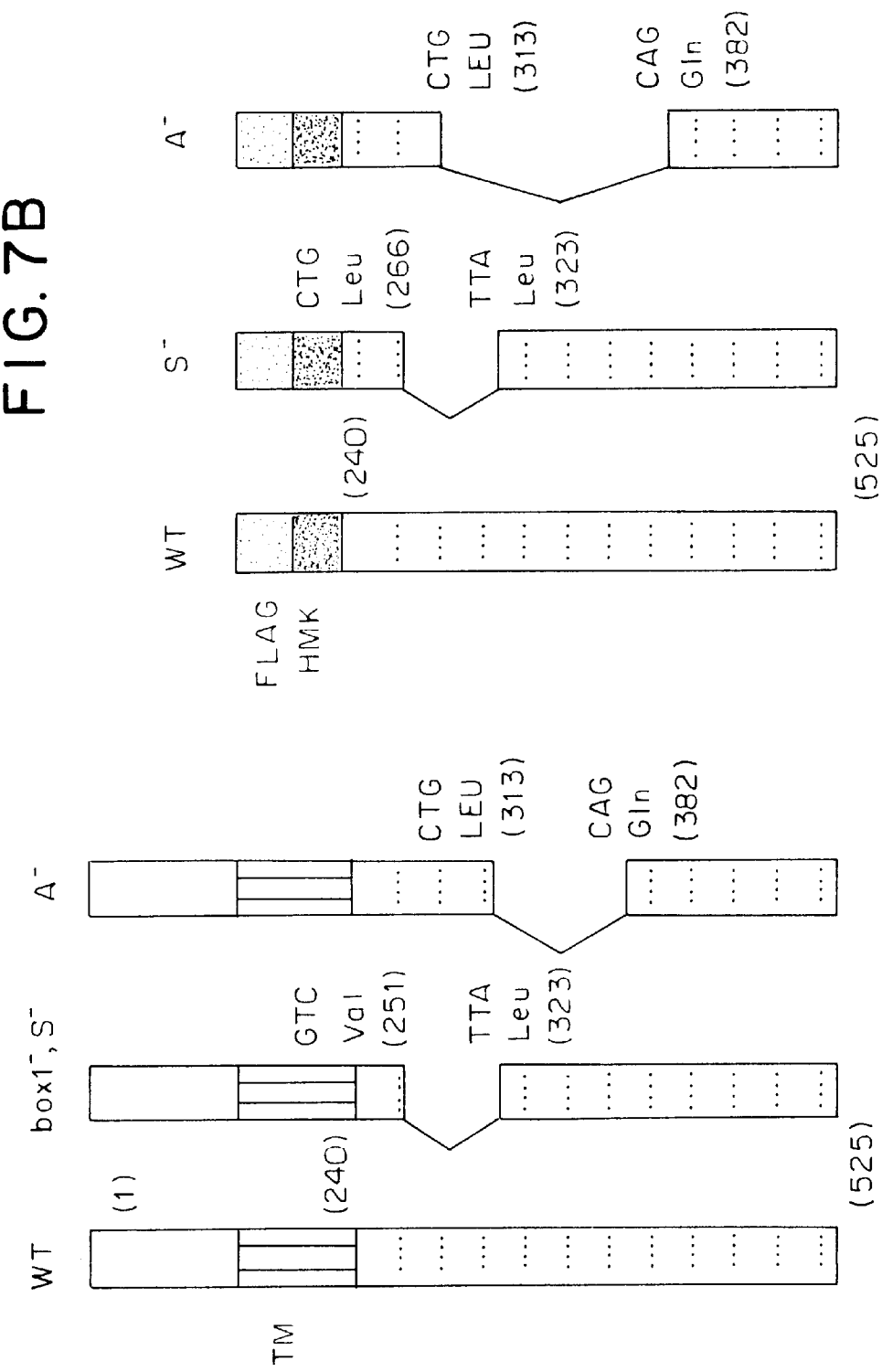

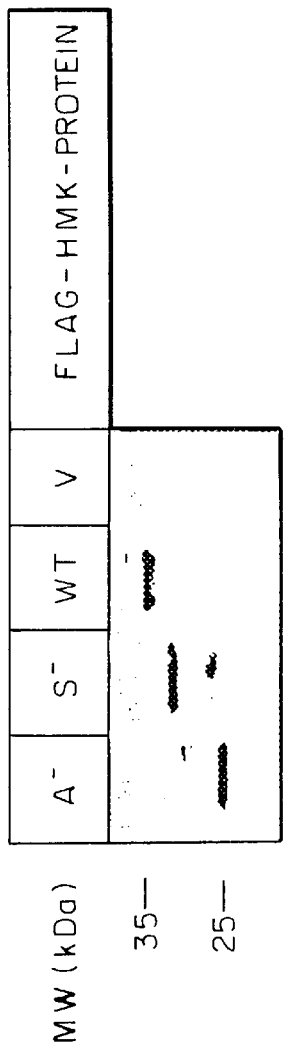

| V | V | WT | WT | S⁻ | S⁻ | A⁻ | A⁻ | AFFINITY BEADS COATED WITH FLAG-HMK-PROTEIN |
|---|---|----|----|----|----|----|----|---------------------------------------------|
|   | + |    | +  |    | +  |    | +  | T-CELL LYSATES                              |
| + |   | +  |    | +  |    | +  |    | LYSIS BUFFER                                |

Raf-1—

|   |   |   |   |   |   | BACTERIAL LYSATES CONTAINING |
|---|---|---|---|---|---|------------------------------|
|   | + |   |   |   |   | FLAG-HMK- VECTOR CONTROL     |
|   |   |   |   | + | + | FLAG-HMK-IL-2Rβ-WT           |
|   |   |   | + | + |   | FLAG-HMK-IL-2Rβ-S⁻           |
|   |   | + | + |   |   | FLAG-HMK-IL-2Rβ-A⁻           |
|   |   |   |   |   |   | (His)₆ - VECTOR CONTROL      |
| + | + | + |   | + | + | (His)₆-Raf-1                 |

Raf-1

FIG. 9
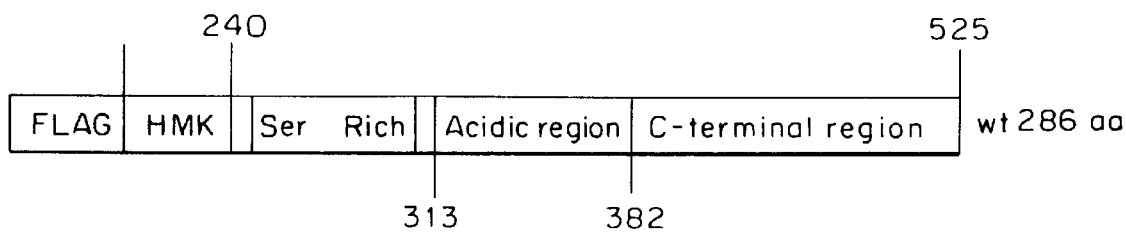
```
H-ras(20)      T I Q L I Q N H F V D E Y D P T I E D S Y R K Q V
               .   : : :       . . .   . : : :     : . .     :
HuIL-2Rβ(371)  A L E I E A C Q V Y F T Y D P Y S E E D P D E G V
```
FIG. 11
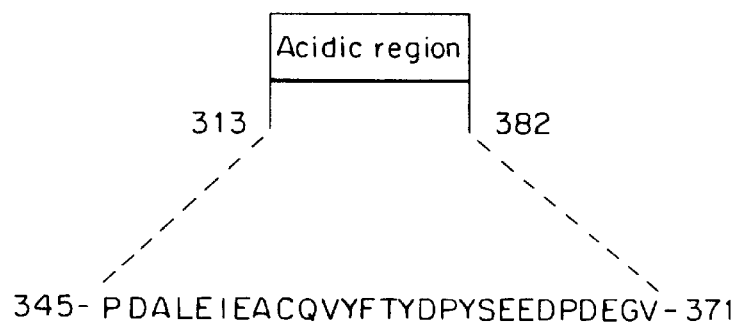
345- P D A L E I E A C Q V Y F T Y D P Y S E E D P D E G V -371

FIG. 10A

| IMMUNOBLOTTING | IP | | | | | | | COS CELLS EXPRESSING |
|---|---|---|---|---|---|---|---|---|
| | Mik-β1 | | | | Control Ab | | | |
| | + | + | + | | + | + | + | IL-2Rβ-WT |
| | + | | | | | + | | p56lck |
| | | + | | | | | + | p59fyn |
| | | | + | | | | + | VECTOR |
| ANTI-Raf-1 | | | | | | | | |
| ANTI-14-3-3 | | | | | | | | |

FIG. 10B

| | | | | | | | AFFINITY COLUMN |
|---|---|---|---|---|---|---|---|
| | | | + | + | + | + | + | FLAG-HMK-IL-2Rβ |
| + | + | | | | | | FLAG-HMK-VECTOR |
| 0 | 20 | 0 | 0.5 | 1 | 2 | 20 | lck (U/ml) |

Raf-1 —

FIG. 10C

| IMMUNOBLOTTING | IP | |
|---|---|---|
| | Control Ab | Mik-β1 |
| ANTI-Raf-1 | | |
| ANTI-14-3-3 | | |
| | − | + | − | + | IL-2 |

FIG. 12

```
-26   maapa l s wr l   pl l i l l l p l a   t s wa sa

1   AVNGTSQFTC   FYNSRAN I SC   VWSQDGALQD   TSCQVHAWPD   RRRWNQTCEL
 51   LPVSQASWAC   NL I LGAPDSQ   KL T TVD IV TL   RVLCREGVRW   RVM A I QDFKP
101   FENLR LMA PI   SLQVVHVETH   RCN I SWE ISQ   ASHYFERH LE   FE AR T LSPGH
151   TWEEAP L LTL   KQKQEWICLE   T LT PDTQ YEF   QVRVKPLQGE   FTTWSPWSQP
201   LA FRTK PAAL   GKDTIPWLGH   L LVGLSGAFG   F I I LVY L L I   239
```

Intracytoplasmic domain

```
                                                  240   N CRNTGPWLKK
251   VLKCNTPDPS   KFFSQLSSEH   GGDVQKWLSS   PFPSSSFSPG   GL A PEI SPLE
301   VLERDKVTQL   LLQQDKVPEP   ASLSS NHSLT   SCFTNQGYFF   F H LPDALE I E
351   ACQVYFTYDP   YSEEDPDEGV   AGAPTGSSPQ   PLQPLSGEDD   AY CTFPSRDD
401   LL LFSPSLLG   GPSPPSTAPG   GSGAGEERMP   PSLQERVPRD   WDPQPLGPPT
451   PGVPDLVDFQ   PPPELVLREA   GEEVPDAGPR   EGVSFPWSRP   PGQGEFRALN
```

SEQUENCE LISTING

```
<160> NUMBER OF SEQ ID NOS: 7

<210> SEQ ID NO 1
<211> LENGTH: 1656
<212> TYPE: DNA
<213> ORGANISM: Homo sapiens
<220> FEATURE:
<221> NAME/KEY: CDS
<222> LOCATION: (1)..(1653)

<400> SEQUENCE: 1 atg gcg gcc cct gct ctg tcc tgg cgt ctg ccc ctc ctc atc ctc ctc      48
Met Ala Ala Pro Ala Leu Ser Trp Arg Leu Pro Leu Leu Ile Leu Leu
  1               5                  10                  15 ctg ccc ctg gct acc tct tgg gca tct gca gcg gtg aat ggc act tcc      96
Leu Pro Leu Ala Thr Ser Trp Ala Ser Ala Ala Val Asn Gly Thr Ser
             20                  25                  30 cag ttc aca tgc ttc tac aac tcg aga gcc aac atc tcc tgt gtc tgg     144
Gln Phe Thr Cys Phe Tyr Asn Ser Arg Ala Asn Ile Ser Cys Val Trp
         35                  40                  45 agc caa gat ggg gct ctg cag gac act tcc tgc caa gtc cat gcc tgg     192
Ser Gln Asp Gly Ala Leu Gln Asp Thr Ser Cys Gln Val His Ala Trp
     50                  55                  60 ccg gac aga cgg cgg tgg aac caa acc tgt gag ctc ctc ccc gtg agt     240
Pro Asp Arg Arg Arg Trp Asn Gln Thr Cys Glu Leu Leu Pro Val Ser
 65                  70                  75                  80 caa gca tcc tgg gcc tgc aac ctg atc ctc gga gcc cca gat tct cag     288
Gln Ala Ser Trp Ala Cys Asn Leu Ile Leu Gly Ala Pro Asp Ser Gln
                 85                  90                  95
```

```
aaa ctg acc aca gtt gac atc gtc acc ctg agg gtg ctg tgc cgt gag        336
Lys Leu Thr Thr Val Asp Ile Val Thr Leu Arg Val Leu Cys Arg Glu
        100                 105                 110 ggg gtg cga tgg agg gtg atg gcc atc cag gac ttc aag ccc ttt gag        384
Gly Val Arg Trp Arg Val Met Ala Ile Gln Asp Phe Lys Pro Phe Glu
    115                 120                 125 aac ctt cgc ctg atg gcc ccc atc tcc ctc caa gtt gtc cac gtg gag        432
Asn Leu Arg Leu Met Ala Pro Ile Ser Leu Gln Val Val His Val Glu
130                 135                 140 acc cac aga tgc aac ata agc tgg gaa atc tcc caa gcc tcc cac tac        480
Thr His Arg Cys Asn Ile Ser Trp Glu Ile Ser Gln Ala Ser His Tyr
145                 150                 155                 160 ttt gaa aga cac ctg gag ttc gag gcc cgg acg ctg tcc cca ggc cac        528
Phe Glu Arg His Leu Glu Phe Glu Ala Arg Thr Leu Ser Pro Gly His
                165                 170                 175 acc tgg gag gag gcc ccc ctg ctg act ctc aag cag aag cag gaa tgg        576
Thr Trp Glu Glu Ala Pro Leu Leu Thr Leu Lys Gln Lys Gln Glu Trp
            180                 185                 190 atc tgc ctg gag acg ctc acc cca gac acc cag tat gag ttt cag gtg        624
Ile Cys Leu Glu Thr Leu Thr Pro Asp Thr Gln Tyr Glu Phe Gln Val
        195                 200                 205 cgg gtc aag cct ctg caa ggc gag ttc acg acc tgg agc ccc tgg agc        672
Arg Val Lys Pro Leu Gln Gly Glu Phe Thr Thr Trp Ser Pro Trp Ser
    210                 215                 220 cag ccc ctg gcc ttc agg aca aag cct gca gcc ctt ggg aag gac acc        720
Gln Pro Leu Ala Phe Arg Thr Lys Pro Ala Ala Leu Gly Lys Asp Thr
225                 230                 235                 240 att ccg tgg ctc ggc cac ctc ctc gtg ggc ctc agc ggg gct ttt ggc        768
Ile Pro Trp Leu Gly His Leu Leu Val Gly Leu Ser Gly Ala Phe Gly
                245                 250                 255 ttc atc atc tta gtg tac ttg ctg atc aac tgc agg aac acc ggg cca        816
Phe Ile Ile Leu Val Tyr Leu Leu Ile Asn Cys Arg Asn Thr Gly Pro
            260                 265                 270 tgg ctg aag aag gtc ctg aag tgt aac acc cca gac ccc tcg aag ttc        864
Trp Leu Lys Lys Val Leu Lys Cys Asn Thr Pro Asp Pro Ser Lys Phe
        275                 280                 285 ttt tcc cag ctg agc tca gag cat gga gga gac gtc cag aag tgg ctc        912
Phe Ser Gln Leu Ser Ser Glu His Gly Gly Asp Val Gln Lys Trp Leu
    290                 295                 300 tct tcg ccc ttc ccc tca tcg tcc ttc agc cct ggc ggc ctg gca cct        960
Ser Ser Pro Phe Pro Ser Ser Ser Phe Ser Pro Gly Gly Leu Ala Pro
305                 310                 315                 320 gag atc tcg cca cta gaa gtg ctg gag agg gac aag gtg acg cag ctg       1008
Glu Ile Ser Pro Leu Glu Val Leu Glu Arg Asp Lys Val Thr Gln Leu
                325                 330                 335 ctc ctg cag cag gac aag gtg cct gag ccc gca tcc tta agc agc aac       1056
Leu Leu Gln Gln Asp Lys Val Pro Glu Pro Ala Ser Leu Ser Ser Asn
            340                 345                 350 cac tcg ctg acc agc tgc ttc acc aac cag ggt tac ttc ttc ttc cac       1104
His Ser Leu Thr Ser Cys Phe Thr Asn Gln Gly Tyr Phe Phe Phe His
        355                 360                 365 ctc ccg gat gcc ttg gag ata gag gcc tgc cag gtg tac ttt act tac       1152
Leu Pro Asp Ala Leu Glu Ile Glu Ala Cys Gln Val Tyr Phe Thr Tyr
    370                 375                 380 gac ccc tac tca gag gaa gac cct gat gag ggt gtg gcc ggg gca ccc       1200
Asp Pro Tyr Ser Glu Glu Asp Pro Asp Glu Gly Val Ala Gly Ala Pro
385                 390                 395                 400 aca ggg tct tcc ccc caa ccc ctg cag cct ctg tca ggg gag gac gac       1248
Thr Gly Ser Ser Pro Gln Pro Leu Gln Pro Leu Ser Gly Glu Asp Asp
                405                 410                 415
```

```
gcc tac tgc acc ttc ccc tcc agg gat gac ctg ctg ctc ttc tcc ccc    1296
Ala Tyr Cys Thr Phe Pro Ser Arg Asp Asp Leu Leu Leu Phe Ser Pro
            420                 425                 430 agt ctc ctc ggt ggc ccc agc ccc cca agc act gcc cct ggg ggc agt    1344
Ser Leu Leu Gly Gly Pro Ser Pro Pro Ser Thr Ala Pro Gly Gly Ser
                435                 440                 445 ggg gcc ggt gaa gag agg atg ccc cct tct ttg caa gaa aga gtc ccc    1392
Gly Ala Gly Glu Glu Arg Met Pro Pro Ser Leu Gln Glu Arg Val Pro
450                 455                 460 aga gac tgg gac ccc cag ccc ctg ggg cct ccc acc cca gga gtc cca    1440
Arg Asp Trp Asp Pro Gln Pro Leu Gly Pro Pro Thr Pro Gly Val Pro
465                 470                 475                 480 gac ctg gtg gat ttt cag cca ccc cct gag ctg gtg ctg cga gag gct    1488
Asp Leu Val Asp Phe Gln Pro Pro Glu Leu Val Leu Arg Glu Ala
                485                 490                 495 ggg gag gag gtc cct gac gct ggc ccc agg gag gga gtc agt ttc ccc    1536
Gly Glu Glu Val Pro Asp Ala Gly Pro Arg Glu Gly Val Ser Phe Pro
                500                 505                 510 tgg tcc agg cct cct ggg cag ggg gag ttc agg gcc ctt aat gct cgc    1584
Trp Ser Arg Pro Pro Gly Gln Gly Glu Phe Arg Ala Leu Asn Ala Arg
            515                 520                 525 ctg ccc ctg aac act gat gcc tac ttg tcc ctc caa gaa ctc cag ggt    1632
Leu Pro Leu Asn Thr Asp Ala Tyr Leu Ser Leu Gln Glu Leu Gln Gly
530                 535                 540 cag gac cca act cac ttg gtg tag                                    1656
Gln Asp Pro Thr His Leu Val
545                 550

<210> SEQ ID NO 2
<211> LENGTH: 551
<212> TYPE: PRT
<213> ORGANISM: Homo sapiens

<400> SEQUENCE: 2

Met Ala Ala Pro Ala Leu Ser Trp Arg Leu Pro Leu Ile Leu Leu
  1               5                  10                  15

Leu Pro Leu Ala Thr Ser Trp Ala Ser Ala Ala Val Asn Gly Thr Ser
                20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
        50                  55                  60

Pro Asp Arg Arg Arg Trp Asn Gln Thr Cys Glu Leu Leu Pro Val Ser
 65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val His Val Glu
            130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190
```

-continued

```
Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
    290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe His
        355                 360                 365

Leu Pro Asp Ala Leu Glu Ile Glu Ala Cys Gln Val Tyr Phe Thr Tyr
    370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
        435                 440                 445

Gly Ala Gly Glu Glu Arg Met Pro Pro Ser Leu Gln Glu Arg Val Pro
    450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
        515                 520                 525

Leu Pro Leu Asn Thr Asp Ala Tyr Leu Ser Leu Gln Glu Leu Gln Gly
    530                 535                 540

Gln Asp Pro Thr His Leu Val
545                 550
```

<210> SEQ ID NO 3
<211> LENGTH: 25
<212> TYPE: PRT
<213> ORGANISM: Homo sapiens

<400> SEQUENCE: 3

```
Thr Ile Gln Leu Ile Gln Asn His Phe Val Asp Glu Tyr Asp Pro Thr
1               5                   10                  15
```

-continued

```
Ile Glu Asp Ser Tyr Arg Lys Gln Val
            20                  25

<210> SEQ ID NO 4
<211> LENGTH: 17
<212> TYPE: DNA
<213> ORGANISM: Sense oligonucleotide

<400> SEQUENCE: 4
catggctgaa gaaggtc                                                    17

<210> SEQ ID NO 5
<211> LENGTH: 17
<212> TYPE: DNA
<213> ORGANISM: Antisense oligonucleotide

<400> SEQUENCE: 5
ttaagacctt cttcagc                                                    17

<210> SEQ ID NO 6
<211> LENGTH: 24
<212> TYPE: DNA
<213> ORGANISM: Sense oligonucleotide

<400> SEQUENCE: 6
aattcaactg caggaacacc gggc                                            24

<210> SEQ ID NO 7
<211> LENGTH: 24
<212> TYPE: DNA
<213> ORGANISM: Antisense oligonucleotide

<400> SEQUENCE: 7
catggcccgg tgttcctgca gttg                                            24
```

US 6,281,193 B1

COMPOUNDS THAT INHIBIT THE BINDING OF RAF-1 OR 14-3-3 PROTEINS TO THE BETA CHAIN OF IL-2 RECEPTOR, AND PHARMACEUTICAL COMPOSITIONS CONTAINING SAME

This application is a national stage filing under 35 USC 371 from PCT/US97/08542, filed May 22, 1997. This application also claims the benefit of U.S. Provisional Application No. 60/018,183, filed May 23, 1996 now abandoned.

FIELD OF THE INVENTION

The present invention concerns compounds such as proteins, peptides and organic compounds which are characterized by their ability to block the interaction between Raf-1 protein and/or 14-3-3 proteins with the intracellular domain of the β chain of the interleukin-2 receptor molecule (IL-2Rβ), and thereby block the intracellular signaling process mediated by IL-2Rβ. The compounds of the invention are intended to inhibit the activity of IL-2 or IL-15 where desired, for example in autoimmune diseases in general, or graft-versus-host reactions in particular. The present invention also concerns in vitro assays for the isolation, identification and characterization of the above compounds, as well as pharmaceutical compositions containing as active ingredient one or more compounds of the invention.

BACKGROUND OF THE INVENTION

Interleukin-2 (IL-2) is a T-cell derived factor that amplifies the response of T cells to any antigen by stimulating the growth of the T cells. Thus, IL-2 is a critical T-cell growth factor which plays a major role in the proliferation of T cells that occurs subsequent to antigen activation, this proliferation resulting in the amplification of the number of T cells responsive to any particular antigen. IL-15 can generally substitute for IL-2 to exert most, if not all, of these activities (Bamford et al., 1994).

The high affinity ($Kd:10^{-11}M$) IL-2 receptor (IL-2R) is composed of at least three non-covalently associated IL-2 binding proteins: the low affinity ($Kd:10^{-8}M$) p55 (α chain) and the intermediate affinity subunits ($Kd:10^{-9}M$) p75 (β chain) and p64 (γ chain) (Smith, K. A., 1988; Waldmann, T. A., 1993). Proliferative signals for the T cells are delivered through high affinity IL-2 receptors consisting of all three subunits, but not via the low affinity site (Robb, R. J. et al., 1984; Siegal, J. P. et al., 1987; Hatakeyama, M. et al., 1989). IL-2Rα, IL-2Rβ, and IL-2Rγ chains have 13, 286 and 86 amino acid intracytoplasmic domains, respectively.

IL-15, a cytokine with many IL-2-like activities, also utilizes the IL-2Rβ as a part of its receptor complex (Giri et al., 1994). This IL-2Rβ dependent signaling process is fundamental to the cellular effects induced by the binding of IL-2 to its receptor (IL-2R) as well as the effects induced by the binding of IL-15 to its receptor. The IL-2Rβ and γ chains, but not the α chain, are essential for IL-2- as well as IL-15-mediated signal transduction (Nakamura, Y. et al., 1994). The 64 kDa IL-2Rγ chain protein is rapidly phosphorylated on tyrosine residues after stimulation with IL-2. The γ chain has also been shown to be a part of other receptor complexes such as the receptor for IL-4 and IL-7 (Noguchi, M. et al., 1993; Russell, S. M. et al., 1993). Absence of the γ chain leads to a severe combined immunodeficiency disease in humans (Noguchi, M. et al., 1993). IL-2Rγ contains sequences from positions 288 to 321 homologous to the Src homology region 2 (SH2) that can bind to phosphotyrosine residues of some phosphoproteins. Another molecule, designated pp97, has been suggested to be the tyrosine kinase physically associated with the IL-2Rγ chain (Michiel, D. F. et al., 1991).

An analysis of cells transformed with a series of IL-2Rβ chain deletion mutants identified a 46 amino acid serine and proline rich intracytoplasmic region of the IL-2Rβ chain (a.a. 267–312), which is crucial for growth promoting signal transduction (Hatakeyama, M. et al., 1989). This same region is crucial for promoting IL-15 mediated effects. Upon stimulation with IL-2, enzymatically active protein tyrosine kinases and, as the laboratory of the present inventors has previously shown (Remillard, B. et al., 1991), the novel lipid kinase, phosphatidyinositol-3-kinase activity blocks proliferation. Cells that express wild-type IL-2Rα and γ chains and mutant IL-2Rβ chains lacking this 46 a.a. region bind and internalize IL-2, but fail to proliferate in response to IL-2 (Hatakeyama, M. et al., 1989). An identical set of circumstances pertains to IL-15 responses. Although the intracytoplasmic domain of the IL-2Rβ and γ chains lacks a protein tyrosine kinase consensus sequence, several cellular proteins are phosphorylated upon tyrosine residues following IL-2 stimulation (Benedict, S. H. et al., 1987; Ferris, D. K. et al., 1989; Saltzmann, E. M. et al., 1988; Asao, H. et al., 1990; Mills, G. B. et al., 1990; Merida, I. and Gaulton, G. N., 1990). IL-2 induced protein tyrosine kinase activity is due, at least in part, to activation of the $p56^{lck}$ (lck), a src-family protein tyrosine kinase. Controversy exists as to whether the serine/proline rich (Fung, M. R. et al., 1991) or an adjacent tyrosine rich "acidic" region (Hatakeyama, M. et al., 1991) of the IL-2Rβ chain is the lck binding site.

IL-2 also stimulates phosphorylation on serine residues of several proteins (Turner, B. et al., 1991; Valentine, M. V. et al., 1991). Raf-1, a serine/threonine kinase, has been identified as a likely signal transducing element for several growth factor receptors (Carroll, M. P. et al., 1990; Morrison, D. K. et al., 1988; Baccarini, M. et al., 1991; Kovacina, K. S. et al., 1990; Blackshear, P. J. et al., 1990; App, H. et al., 1991). The Raf-1 molecule has a molecular weight of 74 kD and can be divided into 2 functional domains, the amino-terminal regulatory half and the carboxy-terminal kinase domains (for review see Heidecker, G. et al., 1991). Raf-1 has been identified as a crucial signal transducing element for ligand activated EPO receptors (Carroll, M. P. et al., 1991). The IL-2Rβ chain and EPO receptors belong to the same family of receptors and share homologies within their cytoplasmic domains (D'Andrea, A. D. et al., 1989). Stimulation of the IL-2R results in the phosphorylation and activation of cytosolic Raf-1 serine/threonine kinase. IL-2R stimulation leads to a 5 to 10 fold immediate/early induction of the c-raf-1 mRNA expression on freshly isolated, resting T cells (Zmuidzinas, A. et al., 1991) and results in up to a 12-fold increase in Raf-1 protein expression. In addition, a rapid increase in the phosphorylation state of a subpopulation of Raf-1 molecules progressively increases through G1.

Enzymatically active Raf-1 appears in the cytosol of IL-2 stimulated CTLL-2 cells (Hatakeyama, M. et al., 1991) and human T blasts (Zmuidzinas, A. et al., 1991). Following IL-2 stimulation, cytosolic Raf-1 molecules are phosphorylated on tyrosine and serine residues (Turner, B. et al., 1991). The laboratory of the present inventors have studied the signaling pathway by which IL-2 signals T cells to begin dividing. In these studies Raf-1 was identified in immunoprecipitates of the IL-2Rβ chain, suggesting that Raf-1 may be involved as an important element in IL-2 signaling. Further, it was determined that prior to IL-2 stimulation, enzymatically active Raf-1 molecules are physically associated with the IL-2Rβ chain and that following stimulation with IL-2, a protein tyrosine kinase phosphorylates Raf-1 thereby leading to translocation of Raf-1 from the IL-2 receptor into the cytosol (Maslinski, W. et al., 1992). Moreover, dissociation of enzymatically active Raf-1 from the IL-2Rβ chain, but not maintenance of IL-2R associated kinase activity, is completely abolished by genistein, a potent tyrosine kinase inhibitor (Maslinski, W. et al., 1992). The above-noted suggested requirement of Raf-1 for IL-2 signaling has been supported by evidence showing that by blocking Raf-1 expression, IL-2 could not induce T cell proliferation in the absence of Raf-1. Thus, from the aforementioned, it is widely accepted that activation of the Raf-1 serine/theonine kinase is critical for IL-2-mediated T-cell proliferation (see also Riedel et al., 1993).

Prior to IL-2 stimulation, several serine, but not tyrosine nor threonine, residues of the IL-2Rβ chain are phosphorylated (Asao, H. et al., 1990). IL-2 induces rapid (i.e., within 10–30 min) phosphorylation of additional serines, tyrosines and threonines (Asao, H. et al., 1990; Hatakeyama, M. et al., 1991). Tyr 355 and Tyr 358 are major, but not exclusive, tyrosine phosphorylation sites of IL-2R (catalyzed by p561$^{lck}$ in Vitro (Hatakeyama, M. et al., 1991)). The phosphorylation sites of the IL-2Rβ chain may play an important role in IL-2Rβ chain signal transduction and interactions with accessory molecules (like p561$^{lck}$ and Raf-1).

Phosphorylation of Raf-1 has also been demonstrated in a human T cell line following CD4 cross-linking. Activation of Raf-1 has also been observed following TCR/CD3 complex stimulation by CD3 or Thy 1 cross-linking as well as an approximately four fold increase in c-raf-1 mRNA. In this case, Raf-1 phosphorylation occurs only on serines and is not observed if PKC had been down regulated. It is interesting to note in this context that GTPase-activating protein (GAP) activation and, consequently, Ras induction following TCR stimulation is also PKC mediated (Downward, J. et al., 1990).

However, the precise residues that form the contact points of p56$^{lck}$ tyrosine kinase, and PI-3-kinase to the IL-2Rβ chain have not been established. Indeed, two groups (Greene and Taniguchi) have utilized grossly truncated IL-2Rβ cDNA transfectants to analyze the binding sites of the IL-2R to lck (Hatakeyama, M. et al., 1991; the Greene group; Turner, B. et al., 1991; the Taniguchi group). Although they used essentially the same techniques and reagents, the conclusions of these studies are conflicting. It is possible that the use of drastically truncated mutants may result in conformational changes in the expressed protein that confound attempts to precisely map the residue to residue contact points required for ligand to ligand interaction. Moreover, recent data from Greene's group is more in line with Tanaguchi's data (Williamson, P. et al., 1994). However, the model cell line used by both laboratories (Baf/3) has been shown to signal differently than a T cell line CTLL2 (Nelson, B. H. et al., 1994). Thus, it is not completely clear which portions of the IL-2Rβ chain are of most importance to normal T cells.

The recent characterization of so-called "knockout" mice for IL-2 (i.e., mice which lack IL2) has shown that about 50% die by nine weeks of age (Schorle, H. et al., 1991). Although these mice appear to be phenotypically normal and can mount some cell-mediated responses (Kundig, T. M. et al., 1993), they ultimately develop inflammatory disease. Recently, it has been suggested that the reason the mice are still relatively normal is that there is an additional cytokine (IL-15) that signals through the IL-2 receptor β and γ chains. Thus, there may be some compensation by IL-15 in these mice for the lack of the IL-2 molecules. On the other hand, deficiency of the IL-2Rγ chain in humans leads to a severe combined immunodeficiency, characterized by the near absence of both mature and immature T cells (Noguchi, M. et al., 1993). Further support for the importance of IL-2 in vivo comes from studies utilizing anti-IL-2 antibodies. Marked immunosuppressive effects in both transplantation and autoimmune models have been obtained by using anti-IL-2Rα monoclonal antibodies (Strom, T. B. et al., 1993). Clinical efforts with similar anti-human IL-2Rα antibodies (produced in mice as monoclonal antibodies) showed some efficacy but this was limited by a rapid immune response in the human patients to the murine monoclonal antibody, i.e., human-anti-mouse antibodies (HAMA) were produced in the patients a short time after treatment with the mouse-anti-human IL-2Rα monoclonal antibodies.

Members of the highly conserved 14-3-3 protein family, first identified as abundant 27–30 kD acidic proteins in brain tissue (Moore et al., 1967) and later found in a broad range of tissues and organisms (Aitken et al., 1992), were recently found to be associated with the products of proto-oncogenes and oncogenes, such as Raf-1, Bcr-Ab1, and the polyoma-virus middle tumor antigen MT (Fu et al., 1994; Reuther et al., 1994; Pallas et al., 1994; Irie et al., 1994; Freed et al., 1994). 14-3-3 appears to associate and interact with Raf-1 at multiple sites, i.e., amino terminal regulatory regions of Raf-1, kinase domain of Raf-1, zinc finger-like region of Raf-1, etc., with primary sites of interaction located in the amino-terminal regulatory domain (Fu et al., 1994; Freed et al., 1994). In comparing sequences of Bcr, Bcr-Ab1 and MT at sites of interaction with 14-3-3, cysteine- and serine-rich regions were found to be common elements and may be some of the determinants responsible for 14-3-3 binding (Morrison, 1994).

The results reported by Freed et al. (1994) and Irie et al. (1994) suggest that 14-3-3 modulates Raf-1 activity in yeast. For instance, Freed et al. (1994) found that over-expression of mammalian 14-3-3 proteins in yeast stimulated the biological activity of mammalian Raf-1, and observed that mammalian Raf-1 immunoprecipitated from yeast strains overexpressing 14-3-3 had three- to four-fold more enzymatic activity than Raf-1 from yeast strains lacking 14-3-3 expression. However, 14-3-3 proteins alone are not sufficient to activate the kinase activity of Raf-1, suggesting that 14-3-3 may be a cofactor involved in Raf-1 activation (Morrison, 1994; Freed et al., 1994). Because 14-3-3 constitutively associates with Raf-1 in vivo regardless of subcellular location or Raf-1 activation state or whether Raf-1 is bound to Ras (Fu et al., 1994; Freed et al., 1994), it is suggested that an alternate function of 14-3-3 may be a structural role in stabilizing the activity or conformation of signaling proteins (Morrison, 1994).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

In view of the above-mentioned differences of the prior art, one of the aims of the present invention has been to determine the nature of interaction between the IL-2Rβ chain and Raf-1 and possibly other proteins or peptides involved in the IL-2- or IL-15-mediated intracellular processes. Accordingly, another aim of the present invention has been to find ways of inhibiting the binding between Raf-1 and IL-2Rβ, and between IL-2Rβ, 14-3-3 and other proteins directly involved in IL-2- or IL-15-mediated intracellular processes, and thereby provide a way in which autoimmune diseases in general, all graft rejection and graft-versus-host reactions may be treated successfully.

The present invention is based on the development of in vitro assay systems to determine the nature and specificity of the binding between Raf-1 and IL-2Rβ chain intracellular domain and the finding that the acidic region of the IL-2Rβ chain is essential for binding of Raf-1 to IL-2Rβ. The binding of IL-2Rβ to Raf-1 is an essential step in the intracellular signaling process mediated by the IL-2R and IL-15R following IL-2/IL-15 stimulation, and is implicated, amongst others, in autoimmune diseases in general, allograft rejection and graft-versus-host reactions in particular.

More specifically, in accordance with the present invention it has now been found that the intracellular domain of the IL-2Rβ chain directly binds to Raf-1 and so-called 14-3-3 proteins. The acidic domain of the intracellular domain of the IL-2Rβ chain, that is homologous to the Ras effector domain, is critical for Raf-1 binding while the C-terminal portion of the intracellular domain of the IL-2Rβ chain interacts with 14-3-3 protein. Further, the Raf-1 and 14-3-3 proteins form complexes on the IL-2Rβ chain intracellular domain and in the presence of enzymatically active $p56^{lck}$, but not $p59^{fyn}$, Raf-1/14-3-3 complexes dissociate from the intracellular domain of the IL-2Rβ chain. Thus, the direct binding of Raf-1/14-3-3 proteins to the intracellular domain of the IL-2Rβ chain by-passes the requirement for membrane localization through activated Ras in other systems.

In view of the above, it thus arises that the co-localization of both Raf-1 together with 14-3-3 on the acid domain and the C-terminal portion of the intracytoplasmic segment of the IL-2Rβ chain is an important step in the intracellular signal transduction process mediated by the IL-2Rβ chain. This interaction is therefore the target for the desired compounds which can disrupt or inhibit this interaction in accordance with the present invention. Such disruption or inhibition of the above interaction provides a specific inhibition of the IL-2/IL-15 initiated intracellular signalling via the IL-2Rβ. Such inhibition is desirable in the treatment of autoimmune diseases in general and graft-versus-host reactions, in particular.

Accordingly, the present invention provides a compound capable of binding to Raf-1 protein, 14-3-3 proteins, or to the intracellular domain of the IL-2Rβ chain and being able to inhibit the binding of Raf-1 and/or 14-3-3 proteins to IL-2Rβ.

Embodiments of this aspect of the invention include: (i) A compound selected from proteins, peptides and analogs or derivatives thereof, and organic compounds; (ii) a compound being the 27 amino acid peptide corresponding to amino acid resides 370 to 396 of SEQ ID NO:2, derived from the acidic region of the mature human IL-2Rβ chain as set forth in FIG. 12 or analogs or derivatives thereof; (iii) a compound being selected from analogs of said 27 amino acid peptide in which one or more amino acid residues have been added, deleted or replaced, said analogs being capable of inhibiting the binding between Raf-1 and/or 14-3-3 and IL-2Rβ.

The present invention also provides a pharmaceutical composition comprising a compound of the invention or a mixture of two or more thereof, as active ingredient and a pharmaceutically acceptable carrier, excipient or diluent.

Further, the present invention provides an in vitro screening assay for isolating, identifying and characterizing compounds according to the invention, capable of binding to Raf-1, 14-3-3 proteins, or IL-2Rβ chain intracellular domain, comprising (a) providing a synthetically produced, a bacterially produced or a mammalian cell produced protein selected from IL-2Rβ chain protein or Raf-1 protein or 14-3-3 protein or portions of any one thereof, or mixtures of any of the foregoing; (b) contacting said protein of (a) with a test sample selected from prokaryotic or eukaryotic cell lysates, a solution containing naturally derived or chemically synthetized peptides, or a solution containing chemically synthetized organic compounds, to form a complex between said protein and said test sample; (c) isolating the complexes formed in (b); (d) separating the test sample from the protein in the complexes isolated in (c); and (e) analyzing said separated test sample of (d) to determine its nature. An embodiment of the above assay is an in vitro screening assay for isolating, identifying and characterizing compounds capable of binding to Raf-1, 14-3-3 proteins or IL-2Rβ chain intracellular domain, as described in Examples 1–6 herein.

Other embodiments of the above screening assay of the invention include an in vitro screening assay wherein said assay is the herein described cell-free assay system; an in vitro screening assay wherein said assay is the herein described totally cell-free assay system; an in vitro assay for screening a compound capable of binding to Raf-1, and/or 14-3-3 proteins or IL-2Rβ intracellular domain and inhibiting the binding between Raf-1 and IL-2Rβ, said assay comprising the steps of determining the protein kinase reaction as described herein in Examples 1–6; as well as compounds isolated, identified and characterized by the in vitro assays according to the invention.

Accordingly, the present invention also provides: (i) compounds isolated, identified and characterized by any of the above in vitro assays; (ii) a pharmaceutical composition for the treatment of autoimmune diseases or graft-versus-host reactions containing a compound of the invention; and (iii) use of a compound of the invention for the treatment of autoimmune diseases transplant rejection or graft-versus-host reactions.

BRIEF DESCRIPTION OF THE DRAWINGS

FIGS. 7(a–c) depict schematically the structure of the IL-2Rβ fusion proteins prepared for expression in mammalian (COS) cells (FIG. 7a, IL-2Rβ chain contructs) and in bacterial cells (FIG. 7b, FLAG-HMK-IL-2Rβ chain constructs), as well as the results of expression of these fusion proteins (FIG. 7c), as described in Example 4;

FIG. 9 depicts a schematic representation of the homology between IL-2Rβ chain (human) (amino acid residues 372 to 396 of SEQ ID NO:2) and the Ras (human) protein (SEQ ID NO:3), as described in Example 4;

FIGS. 10(a–b) depict the results illustrating the abrogation by enzymatically active p56$^{lck}$ of Raf-1 and 14-3-3 binding to the IL-2Rβ chain, as described in Example 4;

FIG. 10c depicts the results illustrating the binding of Raf-1 and 14-3-3 proteins from T-cell lysates to the IL-2Rβ chain as described in Example 4.

FIG. 11 is a schematic illustration of the determination of the Raf-1/IL-2Rβ chain contact points as described in Example 5; and FIG. 12 is a schematic representation of the amino acid sequence of the human IL-2Rβ chain (SEQ ID NO:2), as described in Example 5. The extracytoplasmic domain is in the upper part of the figure in upper case letters. The peptide leader is indicated by lower case letters and the transmembrane region by underlined letters. The acidic region (aa 313–382) is indicated by dashed underlined letters and the putative region (aa 345–371) involved in IL-2Rβ/Raf-1 interaction is shown by italic letters.

DETAILED DESCRIPTION OF THE INVENTION

Figure 1:
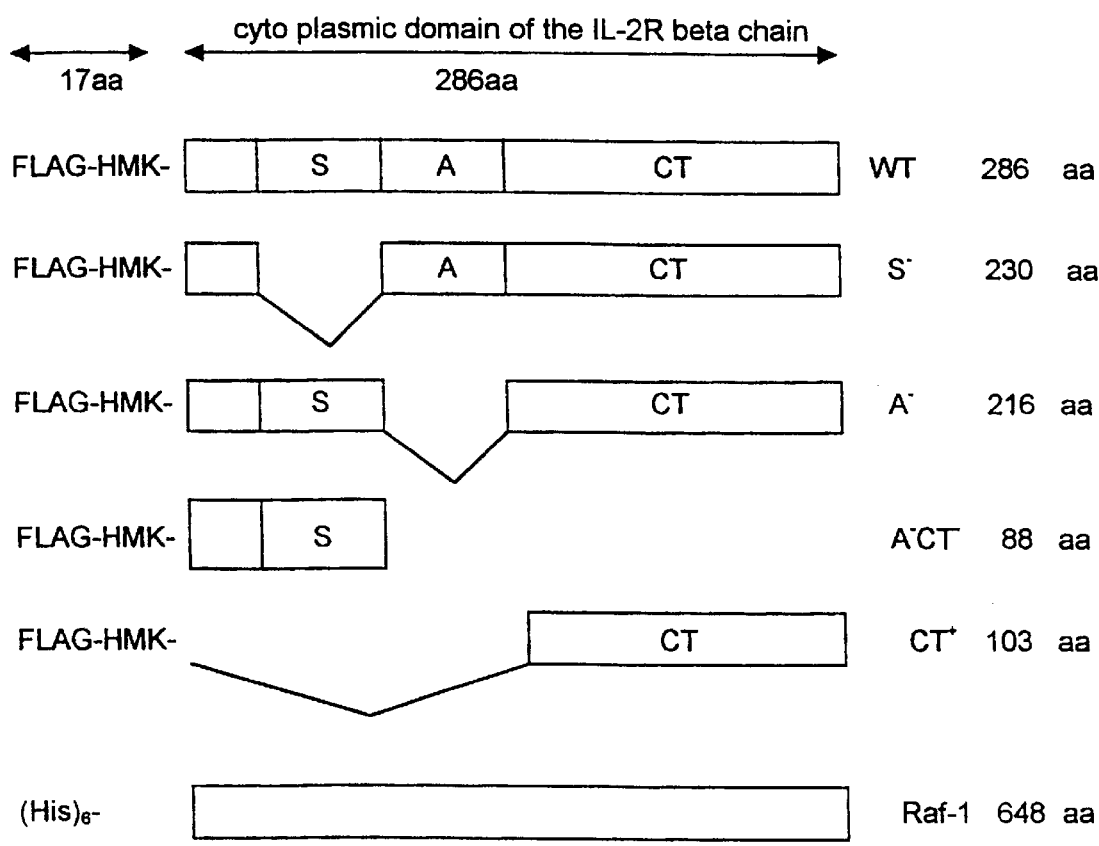
FIG. 1 depicts schematically the structure of the IL-2Rβ fusion proteins as described in Example 1.

The present invention will now be described in more detail in the following non-limiting examples and accompanying figures:

EXAMPLE 1

IL-2Rβ Chain Interaction with Raf-1 Proteins: the IL-2Rβ Chain Region Involved in Raf-1 Binding As mentioned hereinabove, the direct interaction of the IL-2Rβ chain and Raf-1 binding has not been previously described. It has been widely believed that the IL-2Rβ mediated activation of Raf-1 involves the intermediacy of other proteins. In addition, it has not previously been determined whether or not 14-3-3 proteins ate capable of binding to the IL-2Rβ chain directly. Again, other intermediate proteins have been implicated in 14-3-3 binding. Furthermore, characterization of the proteins that are associated with the IL-2Rβ chain is limited by the low copy number of receptors per T cell (2–3×10$^3$ receptors/cell), complexity of the interactions between the receptor protein and the myriad of associated proteins.

Accordingly, there has been developed in accordance with the present invention, a cell-free system in order to analyze the interaction between the IL-2Rβ chain and Raf-1 and/or 14-3-3 proteins, in particular, to identify the region(s) of the IL-2Rβ chain essential for binding to Raf-1 and/or 14-3-3 proteins. The binding of the 14-3-3 proteins to IL-2Rβ is set forth in Example 4. This cell-free system was initially prepared as follows:

(i) The IL-2Rβ chain cytoplasmic domain was cloned in a bacterial expression system and expressed as part of a fusion protein downstream from 17 hydrophilic amino acids comprising an antigenic epitope (FLAG) and a recognition site for heart muscle kinase (HMK) that permits in vitro radiolabeling of the fusion protein with [γ$^{32}$P]-ATP and HMK (LeClair, K. P. et al., 1992; Blanar, M. A. and Rutter, R. J., 1992). The FLAG-HMK-IL-2Rβ chain cytoplasmic domain expression plasmid was constructed by ligating the appropriate 1107 bp (NcoI-BamHI) cDNA fragment from the IL-2Rβ chain into the FLAG-HMK vector (LeClair et al., 1992; Blanar and Rutter, 1992) using synthetic linkers that facilitated cloning and maintain the proper translational frame. BL-21 pLysS bacteria were transformed with the FLAG-HMK-IL-2Rβ construct, and protein expression was induced as described (LeClair et al., 1992).

(ii) In order to study the interaction of IL-2Rβ chain with intracellular molecules, the FLAG-HMK-IL-2Rβ chain cytoplasmic domain fusion protein was purified from bacterial lysate using the M2 anti-FLAG monoclonal antibody in a standard affinity chromatography procedure. More specifically, bacterial lysate proteins were absorbed onto anti-FLAG (M2) affinity column (IBI-Kodak, New Haven, Conn., USA). After washing the column, the adsorbed proteins were eluted with either glycine buffer (pH 3) or FLAG peptide (10$^{-4}$M). Proteins in various fractions were analyzed for expected size (about 33 kDa) and purity after separation on SDS-PAGE and Commassie blue staining. The presence of a functional HMK recognition site was confirmed by phosphorylation of the purified 33 kDa IL-2Rβ chain fusion protein by HMK. More specifically, the eluted fusion proteins were tested for susceptibility to phosphorylation by incubation with the catalytic subunit of bovine heart muscle kinase (Sigma) (1 U/ul) in buffer containing 20 mM Tric-HCl, pH 7.5, 1 mM DTT, 100 mM NaCl, 10 mM MgCl$_2$ and 1 $\mu$Ci [(γ$^{32}$P] ATP for 30 min at 37° C. followed by SDS-PAGE and autoradiography. Purified FLAG-HMK-IL-2Rβ chain fusion proteins were used as an affinity reagent to probe for cytosolic proteins present in lysates of human T cells, metabolically labeled with [$^{35}$S]-methionine, that bind to the IL-2Rβ chain. The human T cells being peripheral blood mononuclear cells were isolated using Ficoll-Hypaque, stimulated with phytohemagglutinin (5 $\mu$g/ml) in culture for 72 h, washed, maintained in culture for 3 days in the presence of IL-2 (10 U/ml), and then incubated without IL-2 for 24 hours. For [$^{35}$S]-methionine labeling, the cells were suspended at 4×10$^7$ cells/ml at 37° C. followed by addition of 0.5 mCi of [$^{35}$S]-methionine for 4 hours prior to lysis in Dounce homogenization buffer and application of the lysate to the affinity column. Several [$^{35}$S]-labeled proteins were retained by the FLAG-HMK-IL-2Rβ chain cytosolic domain fusion protein bound to the affinity column. One of these proteins was identified as Raf-1 by immunoblotting using a polyclonal antibody specific for the SP-63 peptide which corresponds to the C-terminal fragment of Raf-1. A molar excess of the competing SP-63 peptide blocked binding of the anti-SP-63 antibody to Raf-1.

(iii) In order to test for serine/threonine kinase activity, proteins eluted from FLAG-HMK or FLAG-HMK-IL-2Rβ chain affinity columns by FLAG peptide were diluted 1:1 in kinase buffer (25 mM HEPES, pH 7.5, 10 mM MgCl$_2$, 1 mM DTT) with or without genistein (10 $\mu$g/ml) and Histone Hi (20 $\mu$g/ml) was added. The kinase reaction was initiated by the addition of 1 $\mu$Ci of [γ$^{32}$P]-ATP and 25 $\mu$M ATP. After 30 min at 24° C., the reaction was stopped by addition of reducing SDS-PAGE sample buffer and boiling. The results showed that there was serine/threonine kinase activity among the human T-cell derived proteins bound to the IL-2Rβ chain affinity column, and this protein kinase activity was not inhibited by treatment with the tyrosine kinase inhibitor, genistein. These results confirmed that IL-2Rβ cytoplasmic domain chain fusion proteins can be used to study the binding of IL-2Rβ chain and cellular Raf-1 serine/threonine kinase in vitro, i.e., in a cell-free system.

Using the basic cell-free system described above, a number of FLAG-HMK-IL-2Rβ chain wild type FLAG-HMK-IL2Rβ chain deletion mutant proteins were then studied with respect to this specific interaction with Raf-1 proteins present in T-cell lysates. These FLAG-HMK-IL2Rβ chain wild type (WT) and deletion mutants lacking certain defined domains of the IL-2Rβ chain were used to identify the IL-2Rβ chain domain involved in Raf-1 binding. Assay conditions were similar to those described above. Briefly, bacterially produced proteins: (a) FLAG-HMK-IL-2Rβ chain wild type (WT); (b) FLAG-HMK-IL-2Rβ chain containing only the proline rich C-terminal (CT$^+$); FLAG-HMK-IL-2Rβ chain mutants lacking; (c) the serine rich region (S$^-$); (d) the acidic domain (A$^-$); (e) both acidic domain and proline rich C-terminal (A$^-$CT$^-$); or (f) FLAG-HMK vector (v) which does not contain IL-2Rβ chain sequences (negative control), were absorbed on anti-FLAG affinity beads and washed. In FIG. 1, there is shown, schematically, all of the constructs, i.e., FLAG-HMK-IL-2Rβ chain fusion proteins produced in transformed bacterial cells and used in this study. These FLAG-HMK- fusion proteins-coated beads were then used as affinity reagents to absorb Raf-1 proteins present in T-cell lysates. T-cell derived proteins bound to FLAG-HMK fusion proteins were then eluted using buffer containing FLAG peptide, separated on SDS-PAGE, transferred onto Immobilon membrane and blotted with anti-Raf-1 antibody.

Figure 2:
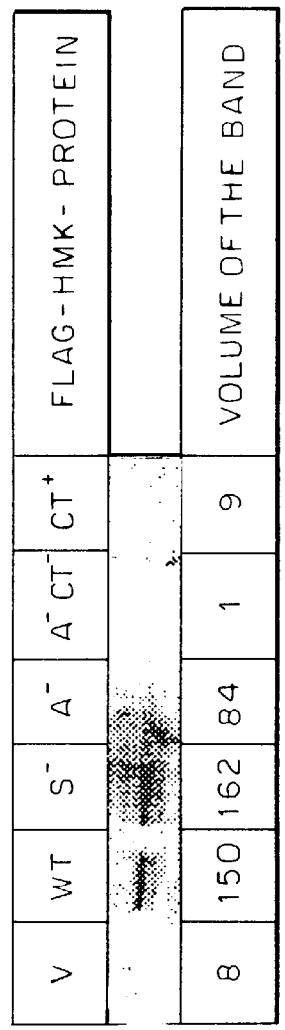
FIG. 2 depicts the results illustrating the binding of Raf-1 from T-cell lysates to FLAG-HMK-IL-2Rβ chain related proteins as described in Example 1.

These experiments were repeated a number of times and the results indicated that: affinity beads coated with FLAG-HMK-IL-2Rβ chain WT or FLAG-HMK-IL-2Rβ chain S-mutant bind T-cell derived Raf-1 proteins equally well; FLAG-HMK-IL-2Rβ chain mutant A$^-$ proteins exhibit diminished binding of Raf-1 proteins (50–80% decrease of Raf-1 binding in comparison to WT control was observed); and there is no binding of Raf-1 proteins to FLAG-HMK-IL-2Rβ chain mutants lacking both acidic and C-terminal domains (mutant A$^-$CT$^-$), FLAG-HMK-IL-2Rβ chain CT$^+$ proteins (i.e. containing only the proline rich C-terminal) or FLAG-HMK vector (V) control. The results of one representative experiment is shown in FIG. 2, which is a reproduction of the relevant bands of an immunoblot of the above noted fusion proteins separated on SDS-PAGE, transferred to the Immobilon membrane and blotted with the anti-Raf-1 antibody. Relative band intensity is apparent from the immunoblot, and the calculated volume of each band corresponding to each different fusion protein is indicated below the band.

EXAMPLE 2

The Interaction of (His)$_6$-Raf-1 Proteins with FLAG-HMK-IL-2Rβ Chain WT and FLAG-HMK-IL-2Rβ Chain Deletion Mutant Proteins In order to study direct interaction of the IL-2Rb chain and Raf-1 proteins two Raf-1 related fusion proteins, i.e., FLAG-HMK-Raf-1 and (His)$_6$-Raf-1 proteins were constructed, bacterially expressed and purified on affinity resins.

For the construction of the FLAG-HMK-Raf-1 expression plasmid, PCR was performed using the Raf-1 cDNA as template and oligonucleotide primers designed to facilitate cloning into the FLAG-HMK-vector (for FLAG-HMK vector, see Example 1). FLAG-HMK-Raf-1 protein was produced in BL-21 pLysS bacteria by IPTG induction, and purified on anti-FLAG affinity resin. Affinity purification yielded a 72–74 kD protein which was recognized by anti-Raf-1 antibody.

For the construction of the (His)$_6$-Raf-1 expression plasmid, PCR was performed using the Raf-1 cDNA as template and oligonucleotide primers designed to facilitate cloning into the pQE-30 plasmid according to the manufacturer's protocol (QIAGEN, QIAexpressionist; Chatsworth, Calif.). (His)$_6$-Raf-1 protein was produced in M15 bacteria by IPTG induction, and purified on Ni-NTA resin (QIAGEN). Affinity purification yielded a 72–74 kD protein which was recognized by anti Raf-1 antibody.

On the basis of the above results, we then analyzed the specific requirements of IL-2Rβ chain regions for binding to Raf-1. In this analysis the above noted cloned, i.e., bacterially produced Raf-1 protein was utilized, the bacterially produced protein being a (His)$_6$-Raf-1 protein as a result of the cloning of the Raf-1 sequence into the expression vector. This has no effect on the Raf-1 activity.

The use of such a bacterially produced (His)$_6$-Raf-1 protein in these binding studies provides yet another advantage over the basic cell-free system in that a totally cell-free system is obtained, i.e., purified bacterially produced IL-2Rβ chain fusion proteins are reacted with purified Raf-1 and not with Raf-1 within a T-cell lysate.

Accordingly, in this totally cell-free assay, FLAG-HMK-IL-2Rβ chain wild type and deletion mutants lacking at least one of several defined domains of the IL-2Rβ chain (see Example 1) were used to identify the IL-2Rβ chain domain involved in Raf-1 binding. Assay conditions were similar to those described in Example 1. Briefly, bacterially produced proteins: FLAG-HMK-IL-2Rβ chain wild type (WT), FLAG-HMK-IL-2Rβ chain containing only proline rich C-terminal (CT$^+$), FLAG-HMK-IL-2Rβ chain mutants lacking:serine rich region (S$^-$), acidic domain (A$^-$), acidic domain and proline rich C-terminal (A$^-$CT$^-$) were incubated with bacterially produced (His)$_6$-Raf-1 (for all constructs see FIG. 1) followed by adsorption of FLAG-HMK-IL-2Rβ chain/Raf-1 complexes on anti-FLAG affinity beads. After extensive washing, IL-2Rβ chain/Raf-1 complexes were competitively eluted from anti-FLAG beads using buffer containing FLAG peptide. Eluted proteins were separated on SDS-PAGE, transferred onto Immobilon membrane and blotted with anti-Raf-1 antibody.

Figure 3:
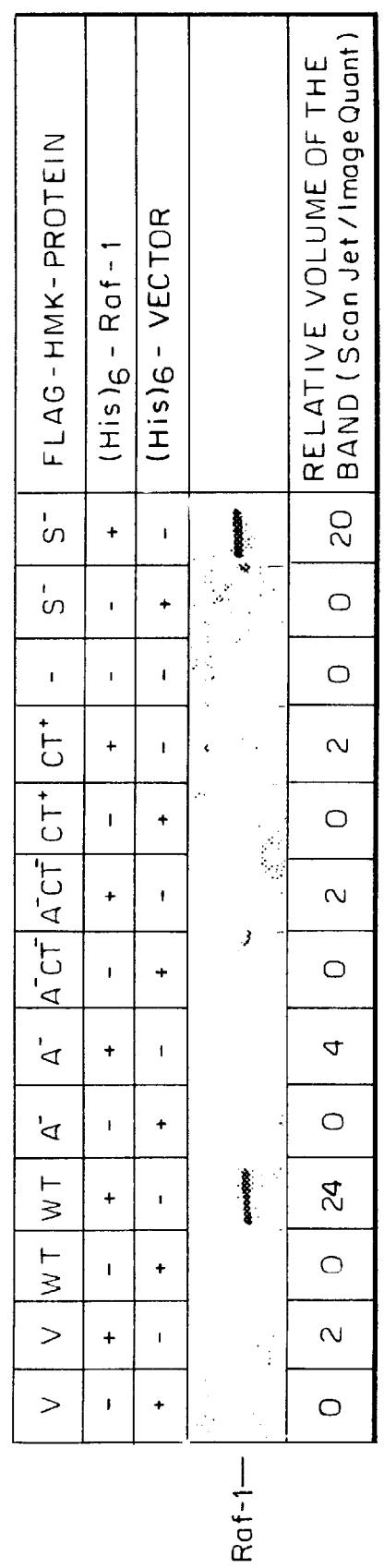
FIG. 3 depicts the results illustrating the interaction between bacterially derived $(His)_6$-Raf-1 proteins with FLAG-HMK-IL-2Rβ chain related proteins as described in Example 2.

The results of one representative experiment is shown in FIG. 3, which is a reproduction of the relevant bands of an immunoblot of the above noted proteins separated on SDS-PAGE, transferred to the Immobilon membrane and blotted with the anti-Raf-1 antibody. Relative band intensity is apparent from the immunoblot and the calculated volume of each band corresponding to each different fusion protein is indicated below the band. It should be noted that in FIG. 3, the two extreme right hand samples, namely the second "WT" and the "VV" are positive and negative controls (see below) and the "+" and "−" signs indicate which IL-2Rβ-FLAG construct was reacted with Raf-1 protein. These experiments were repeated a number of times, essentially with the same results:

(i) FLAG-HMK-IL-2Rβ chain (WT) and deletion mutant lacking the serine rich region (S$^-$) of the IL-2Rβ chain bind Raf-1 proteins equally well. (ii) In contrast, mutants lacking the acidic domain of IL-2Rβ chain (A$^-$) express a significantly reduced capacity to bind Raf-1. The amount of Raf-1 proteins bound to FLAG-HMK-IL-2Rβ A$^-$ mutant as estimated using Hewlett Packard ScanJet varied between 17% to 50% of the positive control value, i.e., 17–50% of Raf-1 binding to FLAG-HMK-IL-2Rβ chain WT. (iii) Mutants lacking both acidic and C-terminal proline rich domains (A⁻CT⁻, also designated FLAG-HMK-IL-2Rβ S⁺, do not bind Raf-1 proteins (0% of the positive control). (iv) FLAG-HMK-IL-2Rβ chain mutant containing only proline rich C-terminal (CT⁺) expressed (0%–10%) binding to Raf-1 proteins. The two negative controls which were carried out were:

1) lysates of bacteria transformed with FLAG-HMK vector (V) alone (no insert) were incubated with equal amount of bacterial lysates containing (His)$_6$-Raf-1 proteins followed by adsorption of proteins onto anti-FLAG beads, washing and elution with buffer containing FLAG peptide. This control sample is at the extreme right hand side of FIG. 3 ("V").

2) Bacterial lysates containing FLAG-HMK-IL-2Rβ chain WT proteins were also incubated with equal amount of lysates prepared from bacteria transformed with vector encoding (His)$_6$-proteins with no insert. This control was undertaken to exclude the possibility that MIS bacteria contain Raf-1-like proteins that may interact with the FLAG-HMK-IL-2Rβ chain proteins. This control sample is second from the extreme right hand side of FIG. 3 (the second "WT").

In view of the above results it is apparent that the acidic domain of the IL-2Rβ chain is required for optimal binding of Raf-1 proteins. It is also possible that a portion of the proline-rich cytoplasmic tail is required for direct binding of Raf-1.

EXAMPLE 3

IL-2Rβ Chain Interaction with Raf-1 Proteins: Serine/Threonine Kinase Activity

The events that lead to activation of Raf-1 serine/threonine kinase in T-cells are unknown. Raf-1 possesses an N-terminal regulatory domain and a C-terminal catalytic domain which are separated by a serine-rich hinge region. It is believed that the regulatory domain folds over the hinge region onto the catalytic domain, thereby suppressing kinase activity (McGrew, B. R. et al., 1992; Bruder, J. T. et al., 1992; Stanton, V. P. et al., 1989). Consistent with this model, N-terminal truncated Raf-1 proteins express constitutive kinase activity (Stanton, V. P. et al., 1989). Binding of the IL-2Rβ to the regulatory domain of Raf-1 may activate the kinase through a conformational change (Maslinski, W. et al., 1992). To determine whether direct binding of Raf-1 to the IL-2Rβ chain induces activation of Raf-1 serine/threonine kinase activity, a FLAG-HMK-Raf-1 fusion protein was constructed and expressed.

In order to test whether direct interaction of IL-2Rβ chain cytoplasmic domain and Raf-1 induces activation of Raf-1 kinase, we utilized a standard serine/threonine kinase assay (see references in Example 1 and 2) to monitor kinase activity of Raf-1 alone and after interaction with the IL-2Rβ chain fusion protein. Neither the purified FLAG-HMK-IL-2Rβ cytoplasmic domain protein nor the FLAG-HMK-Raf-1 protein alone expressed serine/threonine kinase activity. Similarly, when both proteins were combined in equimolar concentrations, serine/threonine kinase activity was not observed. These results indicate that (i) direct interaction of the IL-2Rβ chain and Raf-1 proteins is not sufficient to activate enzymatic activity of Raf-1 and (ii) other factor present in T-cells may be required for mediating Raf-1 kinase activity. In order to test the later notion, using the above noted approach, serine/threonine kinase activity as a result of FLAG-HMK-IL-2Rβ chain interaction with T-cell derived proteins, which included Raf-1, was studied.

(a) Using the above noted approach, serine/threonine kinase activity as a result of FLAG-HMK-IL-2Rβ chain interaction with T-cell derived proteins, which included Raf-1, was studied.

FLAG-HMK-IL-2Rβ chain wild type and deletional mutants lacking certain defined domains of the IL-2Rβ chain (see Examples 1 and 2 and FIG. 1) were used to identify IL-2Rβ chain domain involved in binding T-cell derived, active serine/threonine kinase. Assay conditions were similar to those noted above. Briefly, bacterially produced proteins: FLAG-HMK-IL-2Rβ chain wild type (WT), FLAG-HMK-IL-2Rβ chain containing only proline rich C-terminal (CT⁺), FLAG-HMK-IL-2Rβ chain mutants lacking:serine rich region (S⁻), acidic domain (A⁻), both acidic domain and proline rich C-terminal (A⁻CT⁻), or FLAG-HMK vector which does not contain IL-2Rβ chain sequences (negative control) (for all constructs see diagram on FIG. 1) were absorbed on anti-FLAG affinity beads and washed. FLAG-HMK-fusion proteins coated beads were further used as affinity reagents to absorb proteins present in T-cell lysates. T-cell derived proteins bound to FLAG-MHK fusion proteins were then tested for serine/threonine kinase activity in the absence or presence of exogenous substrates: Histone H-1 or (His)$_6$-Mek-1. Products of kinase reactions were boiled in SDS-PAGE sample buffer followed by separation on SDS-PAGE, transfer onto Immobilon membrane and autoradiography.

The following are the experiments that were carried out and their results:

(i) Kinase reaction performed in the absence of exogenously added substrate. Affinity beads coated with FLAG-HMK-IL-2Rβ chain (WT) or FLAG-HMK-IL-2Rβ chain S⁻-mutant (S⁻) bind T-cell derived protein(s) expressing serine/threonine kinase activity as reflected by phosphorylation of p70 protein. This protein may be Raf-1 insofar as it comigrates with Raf-1 protein. In contrast, there is no phosphorylated band p70 in T-cell lysates retained on beads coated with other FLAG-MHK-IL-2Rβ chain related fusion proteins (mutants A⁻, A⁻CT⁻, CT⁺) or bacterial lysates containing vector (V) control. These experiments were repeated a number of times with essentially the same results. The results of one representative experiment is shown in FIG. 4, which is a reproduction of an autoradiogram of the products of the protein kinase reaction performed on anti-FLAG beads coated with the various IL-2Rβ fusion products, incubated with T cell lysates and subsequently subjected to SDS-PAGE and autoradiography.

Figure 5:
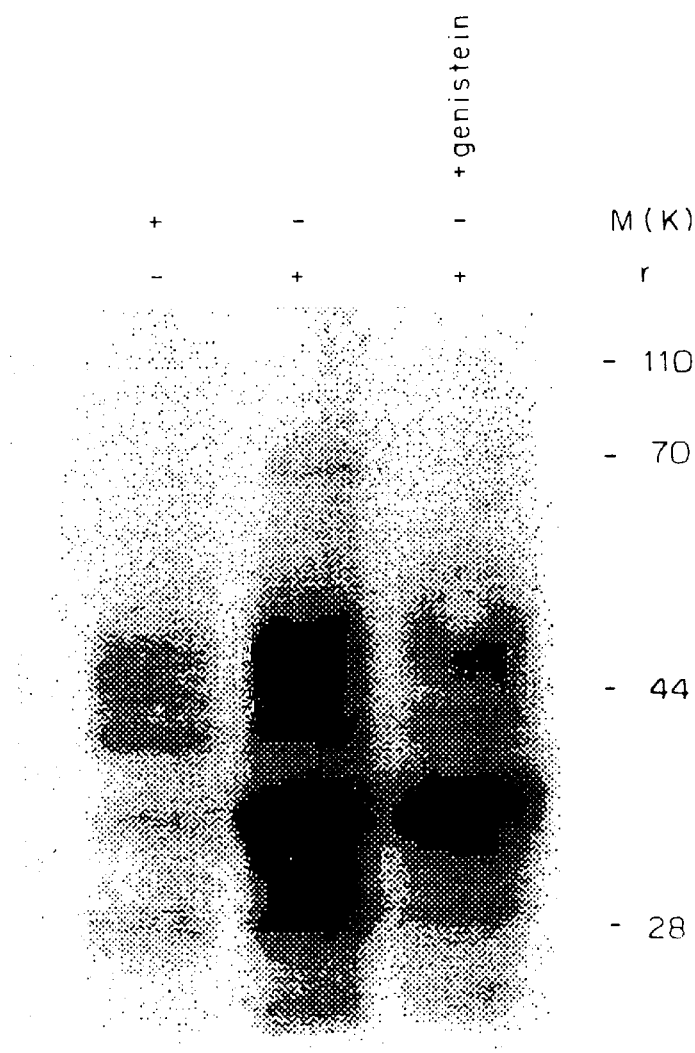
FIG. 5 depicts the results illustrating the products of serine/threonine kinase reaction performed on anti-FLAG beads coated with FLAG-HMK-IL-2Rβ chain and exposed to T-cell lysates, as described in Example 3.

(ii) Kinase reaction Performed in the presence of Histone-H-1. There is an increased, genistein (tyrosine kinase inhibitor) -independent phosphorylation of Histone-H-1 in T-cell lysates retained on affinity beads coated with FLAG-HMK-IL-2Rβ chain. Control affinity beads coated with proteins isolated from bacteria transformed with vector alone and exposed to T-cell lysates retain only background level of serine/threonine kinase activity. These experiments were repeated a number of times. The results of a representative experiment are shown in FIG. 5 which is a reproduction of an autoradiogram of the products of the kinase reaction performed, in the presence of Histone H-1, on anti-FLAG beads coated with the IL-2Rβ chain construct (WT) and exposed to T-cell lysates in the presence of genistein (lane 3), or in the absence of genistein (lane 2) and then subjected to SDS-PAGE and autoradiography. The control (lane 1) was carried out with the FLAG-HMK vector alone (no insert).

(iii) Kinase reaction performed in the presence of kinase defective $(His)_6$-Mek-1 proteins. An increase of the level of $(His)_6$-Mek-1 kinase phosphorylation was observed in the presence of anti-FLAG beads coated with FLAG-HMK-IL-2Rβ chain WT and S⁻ and exposed to T-cell lysates. Background levels of (His)6-Mek-1 kinase phosphorylation were observed in the presence of anti-FLAG beads coated with other FLAG-MHK-IL-2Rβ chain related mutants (mutants A⁻, A⁻CT⁻, CT⁺) or bacterial lysates containing vector control. The results of a representative experiment are shown in FIG. 6 which is a reproduction of an autoradiogram of the products of the kinase reaction performed, in the presence of $(His)_6$-Mek-1 proteins, on various IL-2Rβ chain constructs exposed to T-cell lysates and then subjected to SDS-PAGE and autoradiography.

Figure 4:
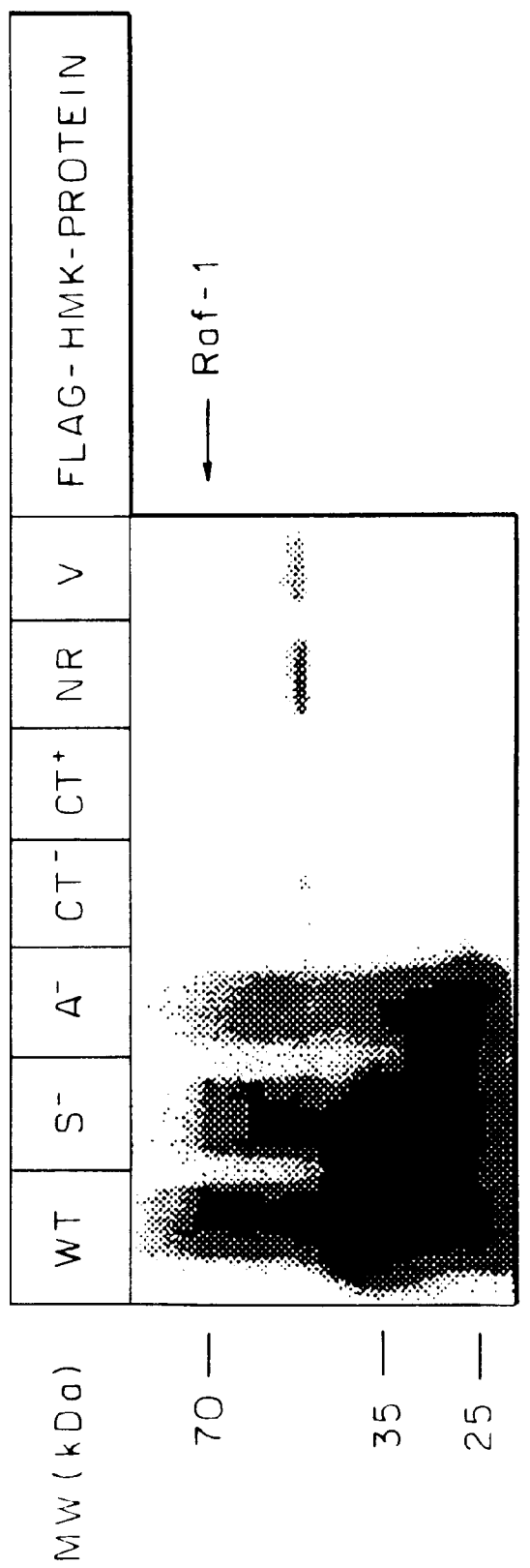
FIG. 4 depicts the results illustrating the products of protein kinase reaction performed on anti-FLAG beads coated with FLAG-HMK-IL-2Rβ chain proteins and exposed to T-cell lysates as described in Example 3.
Figure 6:
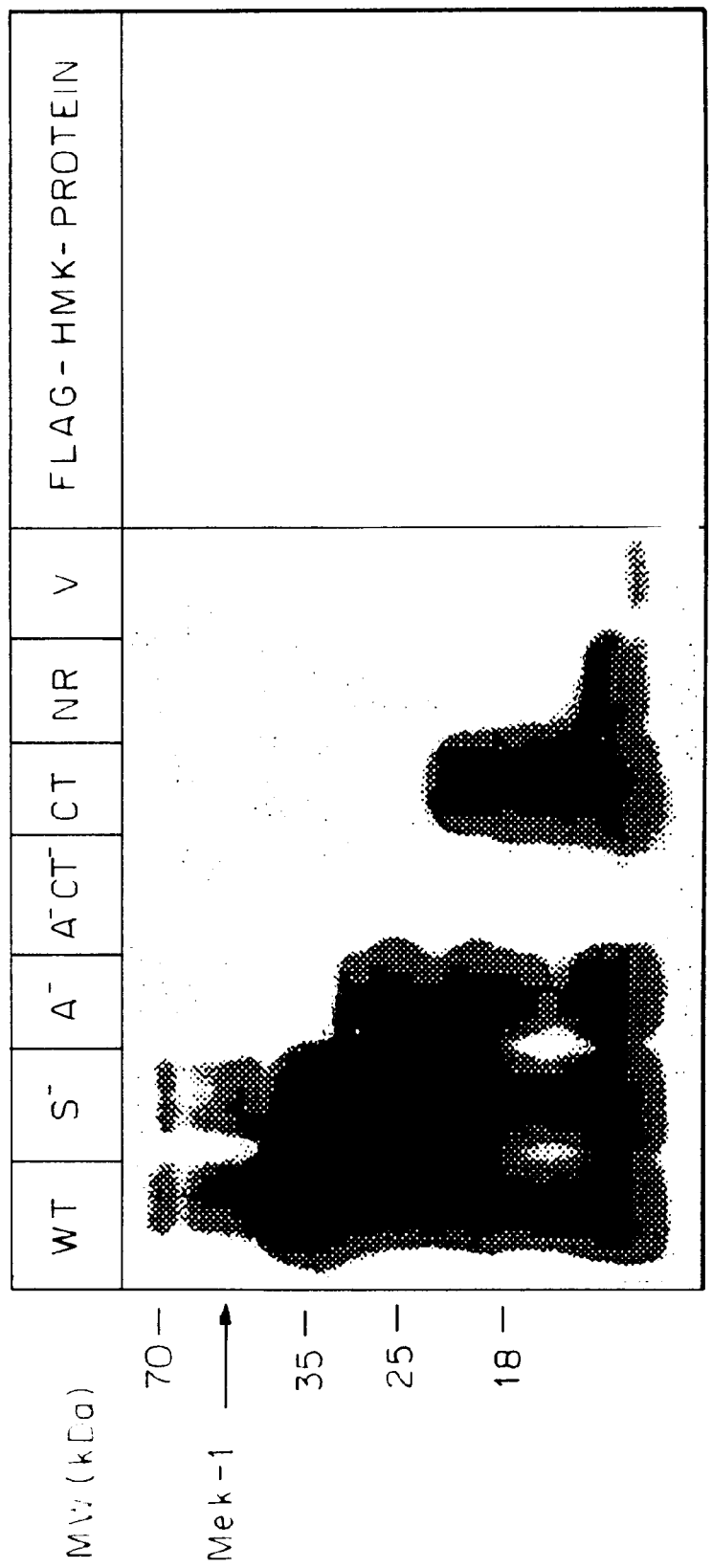
FIG. 6 depicts the results illustrating the products of protein kinase reaction performed on anti-FLAG beads coated with FLAG-HMK-IL-2Rβ chain related proteins and exposed to T-cell lysates, as described in Example 3.

From the results shown in FIGS. 4–6, it is apparent that anti-FLAG affinity beads coated with FLAG-HMK-IL-2Rβ chain wild type (WT) or FLAG-HMK-IL-2Rβ chain mutant lacking serine-rich region (mutant S⁻) and exposed to T-cell lysates, retain active serine/threonine kinase that (i) phosphorylates p70 band which comigrates with Raf-1 proteins, and (ii) phosphorylates kinase inactive $(His)_6$-Mek-1 proteins. In parallel experiments, carried out in the presence of other FLAG-HMK-IL-2Rβ chain related proteins (mutants A⁻, A⁻CT⁻, CT⁺) or bacterial lysates containing vector control, these kinase activities are absent. Taken together these results indicate that enzymatically active serine/threonine kinase Raf-1 binds to the acidic region of the IL-2Rβ chain.

(b) Following on the approach taken in (a) above, serine/threonine kinase activity as a result of FLAG-HMK-IL-2Rβ chain interaction with bacterially produced $(His)_6$-Raf-1 proteins, was studied. As noted in Example 2 above, this totally cell-free system has advantages over the cell-free system in (a) above in which T-lysates were used containing the Raf-1 proteins.

Bacterial lysates containing FLAG-HMK-IL-2Rβ chain wild type and $(His)_6$-Raf-1 proteins were used (see Example 2) to test the hypothesis that the IL-2Rβ chain induces catalytic activity of Raf-1. Assay conditions were similar to those described above. Briefly, bacterially produced proteins: FLAG-HMK-IL-2Rβ chain wild type (WT) or FLAG-HMK (negative control) (for all constructs see FIG. 1) were incubated with bacterial lysates containing either $(His)_6$-Raf-1 or (His), (negative control) followed by the absorption of protein complexes on anti-FLAG affinity beads. Washed beads were tested for the presence of serine/threonine kinase activity in the presence of the exogenously added substrate, enzymatically inactive $(His)_6$-Mek-1 kinase protein. Products of kinase reactions were boiled in SDS-PAGE sample buffer followed by separation on SDS-PAGE, transfer onto Immobilon membrane and autoradiography. These experiments were repeated a number of times with similar results: interaction of FLAG-HMK-IL-2Rβ chain with $(His)_6$-Raf-1 proteins did not result in the induction of kinase activity toward Mek-1 kinase.

These results therefore indicate the possibility that some other factor (or co-factor) is necessary for mediating the Raf-1 kinase activity, this being present in the T cell lysates (see (a) above) but not in the more purified $(His)_6$-Raf-1 preparation from transformed bacterial cells. It is possible that proteins of the 14-3-3 family are involved by binding to Raf-1 and thereby mediate its activity. Such 14-3-3 family proteins have recently been described (Freed et al., 1994; Irie et al., 1994; Morrison, 1994), and these have been studied as set forth in Example 4 below.

EXAMPLE 4

IL-2Rβ Chain Interaction with Raf-1 and/or 14-3-3 Proteins: the IL-2Rβ Chain Region Involved in Raf-1 and/or 14-3-3 Protein Binding In another set of experiments to identify the IL-2Rβ chain domain(s) that might interact with Raf-1 and/or 14-3-3proteins, cDNAs encoding the IL-2Rβ chain or mutants lacking segments of its cytoplasmic domain were prepared and expressed in COS cells.

(i) In these experiments (see also Example 1 a (i) and (ii) above) cDNA encoding human IL-2Rβ chain wild type (IL-2Rβ-WT) (Hatakeyama et al., 1989), was digested with Xba I and inserted into expression vector pRcCMV (Invitrogene). A cDNA encoding mutant IL-2Rβ lacking 71 amino acids (aa 252–322), that contain box 1 (Murakami et al, 1991) and serine rich region critical for signal transduction (Hatakeyama et al., 1989) IL-2Rβ-box 1⁻S⁻, was made by cloning the full length wild type IL-2Rβ chain cDNA (SEQ ID NO:1) into the XbaI site of pBluescript II SK (Stratagene). This construct was then digested with NcoI-AflII. The NcoI/AflII sites were ligated with double stranded linker composed of oligonucleotides:

5'CATGGCTGAAGAAGGTC3' (sense, bases 946–962; SEQ ID No:4) and

5'TTAAGACCTTCTTCAGC3' (antisense, bases 950–962, plus an AflII site; SEQ ID No:5). This construct was then digested with XbaI and fragment containing sequences encoding IL-2Rβ chain was cloned back into pRcCMV. For the construction of IL-2Rβ-A⁻ mutant, pRcCMV-IL-2Rβ was digested with XbaI and cloned into XbaI site of pTZ19R (Pharmacia). This construct was then digested with NcoI-BstXI. The 964 bp fragment containing sequences encoding most of the cytoplasmic domain of the IL-2Rβ chain was replaced with a 754 bp fragment obtained from NcoI and BstXI digestion of the AR(DRI)59/60 plasmid (Le Clair et al., 1992; Blanar et al., 1992) containing FLAG-HMK-IL-2Rβ-A⁻ mutant encoding cDNA (see below). The resultant pTZ-IL-2Rβ-A⁻ plasmid contains sequences encoding an IL-2Rβ chain but lacking 210 bases encoding acidic domain was then digested with XbaI, and a fragment containing sequences encoding IL-2Rβ-A⁻ was cloned back into pRcCMV.

For the construction of plasmid FLAG-HMK-IL-2Rβ chain cytoplasmic domain wild type (FLAG-HMK-IL-2Rβ-WT), a 1107 bp cDNA (see also (i) above) was excised from IL-2Rβ chain cDNA with NcoI-BamHI and ligated with synthetic, in frame double stranded linker EcoRI/NcoI (made from oligonucleotides: sense 5'AATTCAACTG-CAGGAACACCGGGC3' (EcoRI site plus bases 927–944; SEQ ID No:6) and antisense 5'CATGGCCCGGTGTTCCT-GCAGTTG3' (bases 927–949; SEQ ID No:7) into the back bone of pAR(DRI) 59/60 plasmid digested with EcoRI-BamHI. For the construction of FLAG-HMK-IL-2Rβ-S⁻ mutant (serine-rich domain is deleted), a plasmid encoding FLAG-HMK-IL-2R WT was digested with Sac-AflII. After filling both ends, the plasmid was blunt end ligated. For construction of FLAG-HMK-IL-2Rβ-A⁻ mutant (acidic domain is deleted), a 1048 bp fragment obtained from SacI-BamHI digestion of FLAG-HMK-IL-2Rβ-WT was further digested with PstI resulting in 3 fragments of 701, 210 and 136 bp. Fragments 701 and 136 were ligated back into the backbone of SacI-BamHI digested FLAG-HMK-IL-2Rβ-WT construct. The authenticity of each of the introduced mutations was confirmed by DNA sequence analysis.

(ii) In FIG. 7a, there are shown schematic representations of the wild type (WT) and mutant (box 1⁻S⁻; A⁻) IL-2Rβ chain protein constructs prepared as above for expression in COS cells. In FIG. 7b, there are shown schematic representations of the wild type (WTO and mutant (S⁻; A⁻) IL-2Rβ chain protein constructs prepared as above (see also Example 1, a(i) and (ii) above) for expression in COS cells. These constructs were introduced into COS cells and bacterial cells and the proteins were expressed, affinity purified from lysates of the cells, the purified proteins were separated on SDS-PAGE and stained with Commassie blue (for basic procedures see also Le Clair et al., 1992; Blanar and Rutter, 1992). The procedure for expression of the constructs in bacterial cells followed by affinity purification, SDS-PAGE separation and Commassie blue staining has been described above (Example 1, a (i) and (ii)). The procedure for expression of the constructs in COS cells followed by SDS-PAGE separation, affinity purification and Commassie staining was as follows:

COS cells were transfected via the DOTAP method (Boehringer-Mannheim, Indianapolis, Ind.) following the manufacturer's instructions. The transfection cocktail contained 5 μg of DNA total and 30 ml of DOTAP in a final volume of 150 ml HBS (25 mM HEPES, pH 7.4 and 100 mM NaCl). The COS cells were grown in DMEM medium supplemented with 10% heat-inactivated fetal calf serum, penicillin/streptomycin, 25 mM HEPES, pH 7.4, and L-glutamine. The COS cells were exposed to the transfection cocktail for 12 hours, washed and subsequently cultured in fresh medium. 24 hours after washing approximately $3 \times 10^6$ cells were harvested and washed twice in chilled PBS. A lysis buffer was prepared and consisted of 150 mM NaCl, 50 mM Tris pH=7.4, 0.5% CHAPS (Pierce), 10% glycerol (Sigma), supplemented with the following protease inhibitors immediately before use: aprotinin (Sigma) 2.5 mg/ml, leupeptin (Boehringer-Mannheim) 2.5 mg/ml; Pepstatin A (Boehringer-Mannheim) 2 mg/ml, PMSF (Sigma) 150 mg/ml, NaF (Sigma) 100 mM and sodium orthovanadate (Sigma) 1 mM. The transfected COS cells were lysed in 0.5 ml of lysis buffer on ice for 10 minutes, and subsequently centrifuged at 12,000×g for 5 minutes, remaining supernatants were collected, and supplemented with pre-immune serum and protein G-agarose beads (BRL-Gibco, Gaithersburg, Md.), which had been previously washed in lysis buffer. The samples were incubated at 4° C. for 30 minutes on a rocker. Supernatants were collected and supplemented with appropriate antibody, and later the protein G-agarose beads were added. Samples were washed 3 times for 15 min. each in lysis buffer and resuspended in Laemmli buffer and subsequently subjected to SDS-PAGE followed by Commassie blue staining for basic procedures (see also Maslinski, et al., 1992).

Antibodies used in the above affinity purification step (with the protein G-agarose beads) included: a rabbit antiserum raised against a 14-3-3 protein expressed in bacteria using standard procedures, this being a polyclonal anti-14-3-3 antibody protein; a rabbit anti-human 14-3-3 antibody that is cross-reactive with bacterial 14-3-3 proteins purchased from Upstate Biotechnology; an anti-Raf-1 (C1) antibody purchased from Santa Cruz Biotechnology; an anti-human IL-2Rβ antibody called Mik-ol (as described in Tsudo et al, 1989 and obtained from M Tsudo, Kyoto, Japan).

In FIG. 7(c), there is shown a reproduction of the relevant bands of a Commassie blue stained, SDS-PAGE separation of affinity purified FLAG-HMK-IL-2Rβ chain related (wild type and mutant) fusion proteins which were expressed in the COS cells.

(iii) To determine the nature of the binding of the IL-2Rβ chain to Raf-1 and 14-3-3 proteins, COS cells were transfected, as set forth hereinabove, with constructs encoding full-length or deletional mutants of the human IL-2Rβ chain, immunoprecipitated with an anti-IL-2Rβ chain antibody Mik-β1 (see (ii) above) and blotted with anti-Raf-1 or anti-14-3-3 antibodies (see (ii) above).

In addition, in order to determine the interaction of the IL-2Rβ chain with Raf-1 and 14-3-3 proteins in T-cells, lysates of phytohemagglutinin (PHA)-activated peripheral blood mononuclear cells were passed through anti-FLAG affinity beads containing purified FLAG-HMK-IL-2Rβ related proteins (see (i) and (ii) above, as well as Examples 1–3). The absorbed proteins were washed, eluted with FLAG peptide and probed for the presence of Raf-1 and 14-3-3 proteins on immunoblots. The peripheral blood mononuclear cells were isolated using Ficoll-Hypaque (Pharmacia), stimulated with PHA (Sigma) 5 mg/ml in culture for 72 hours, washed, maintained in culture for 3 days in the presence of IL-2 (Hoffman-La Roche) 10 U/ml, and then incubated without IL-2 for 24 hours. Washed cells (about $4 \times 10^7$) were lysed in Dounce homogenization buffer, centrifuged ($15 \times 10^3 \times g$ for 15 min.) and supernatants applied onto washed anti-FLAG (M2) affinity column (IBI-Kodak) coated with bacterial lysates interacted with one of the FLAG-HMK fusion proteins. After washing with 15 ml of buffer containing 50 mM Tris pH=7.4, 150 mM NaCl, proteins adsorbed onto the anti-FLAG affinity column were eluted with the same buffer supplemented with FLAG peptide ($10^{-4}$ M) and subjected to SDS-PAGE and immunoblotting described hereinabove.

To study the IL-2Rβ chain/Raf-1 interaction in vitro, bacterial lysates containing FLAG-HMK-IL-2Rβ chain related and $(His)_6$ Raf-1 fusion proteins (see also Examples 2, 3 above) were mixed and adsorbed on anti-FLAG beads. The proteins bound on the beads were washed, eluted with FLAG peptide and probed for the presence of Raf-1 and 14-3-3 proteins by immunoblotting.

Figure 8B:
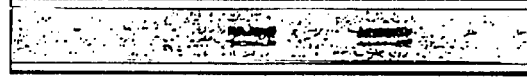
FIGS. 8(a–c) depict the results illustrating the direct interaction between Raf-1 and 14-3-3 proteins with IL-2Rβ chain or portions thereof, as described in Example 4.
Figure 8C:
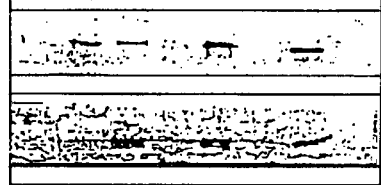

The results of the above experiments are shown in FIGS. 8a–c:

In FIG. 8a, there is shown a reproduction of immunoblots performed on lysates from transfected COS cells which were transfected with the various constructs IL-2Rβ-WT, IL-2Rβ-box 1⁻S⁻, IL-2Rβ-A⁻, or, as a control, a vector having no IL-2Rβ construct (vector). The COS cell lysates were immunoprecipitated with anti-Raf-1 or anti-14-3-3 antibodies. From the results shown in FIG. 8a it is apparent that both IL-2Rβ-WT and the IL-2Rβ-box 1⁻S⁻ mutant bound both Raf-1 and 14-3-3 proteins. In contrast, the IL-2Rβ chain A⁻ mutant failed to bind Raf-1 and bound only 14-3-3 proteins.

In FIG. 8b, there is shown a reproduction of an immunoblot performed on lysates from PHA activated peripheral blood mononuclear cells, which were passed through anti-FLAG affinity beads containing purified FLAG-HMK-IL-2Rβ related proteins. The adsorbed proteins were washed, eluted with FLAG peptide and probed for the presence of Raf-1 and 14-3-3 on immunoblots. From the results shown in FIG. 8b, it is apparent that the same specific interactions (as in FIG. 8a) also occurred when T-cell lysates were passed through IL-2Rβ chain-derived affinity columns, i.e., IL-2Rβ-WT and the IL-2Rβ-box 1⁻S⁻ mutant but not the IL-2Rβ chain A⁻ mutant bound to Raf-1. In these T-cell lysates the Raf-1 protein is at basal levels as shown by phosphorylation of exogenously added kinase inactive MEK protein (see Examples 2 and 3 above).

In view of the results shown in FIGS. 8a and 8b, it was concluded that the 70 amino acidic region (A⁻ region) of the IL-2Rβ chain is required for Raf-1 binding, while the 144 amino acid C-terminal portion of the IL-2Rβ chain is required for interaction with 14-3-3 proteins.

(iv) In order to ascertain whether the A⁻ region and C-terminal regions directly bind to Raf-1 and 14-3-3 proteins respectively, a series of bacterially expressed FLAG- IL-2Rβ chain fusion proteins were tested. In these experiments bacterially expressed (His)6 Raf-1 protein was used (see Examples 2 and 3 above, and FIG. 7b for bacterial constructs). The results of these experiments are shown in FIG. 8c which is a reproduction of an immunoblot performed on bacterial lysates containing FLAG-HMK-IL-2Rβ chain related and (His)6 Raf-1 fusion proteins, which were mixed and adsorbed on anti-FLAG beads. The proteins bound to the beads were washed, eluted with FLAG peptide and probed by immunoblotting. Since the bacterial lysates contained a 28 kD protein, immunoreactive with antibody raised against a highly conserved region of the 14-3-3 protein (residues 119–129 of human 14-3-3) no attempt was made to co-express human 14-3-3 proteins. As is apparent from FIG. 8c, there is direct binding between Raf-1 and the acidic region of the IL-2Rβ chain. Further, as in COS cells, 14-3-3 proteins present in bacterial lysates bound directly to the C-terminal portion of the IL-2Rβ chain. Thus, it appears that the homology between mammalian and bacterial 14-3-3 proteins is sufficient to preserve the 14-3-3 binding site to Raf-1 and the IL-2Rβ chain.

However, it must be also noted that, as arises from FIG. 8c, bacterial 14-3-3 bound to the IL-2Rβ chain only in the presence of Raf-1 proteins. Accordingly, it is likely that Raf-1 and 14-3-3 form a complex before binding to the $A^-$ region (Raf-1) and the C-terminal part (14-3-3) of the IL-2Rβ chain. Once the 14-3-3 protein is bound to IL-2Rβ the requirement to maintain the association with Raf-1 is less stringent as arises from the fact that the mutant IL-2Rβ protein lacking the acidic region does not bind Raf-1 (FIGS. 8b and c).

The above results therefore suggest that Raf-1 plays a central role in these three molecular interactions (Raf-1—14-3-3 - IL-2Rβ). This notion is further supported by the observation that the $A^-$ region of the IL-2Rβ chain is homologous to the effector domain or Ras and Rap1A that binds to Raf-1 (see, for example, Zhang et al., 1993; Nassar et al., 1995). The homology between Ras (H-Ras) and the A region of IL-2Rβ is depicted schematically in FIG. 9. The interaction between IL-2Rβ chain (amino acids 371–395) may therefore be a key factor in Raf-1 immobilization through the IL-2Rβ chain at the plasma membrane.

(v) Triggering of the IL-2 receptor complex activates several tyrosine kinases in T cells; these include Jak-1 (Miyazaki et al., 1994; Jak-3 (see, for example, Johnstein et al., 1994) and p56$^{lck}$ (Minami et al., 1995). Previously, we showed that tyrosine kinase dependent dissociation of Raf-1 from the IL-2Rβ chain is a prerequisite for Raf-1 activation by IL-2 (Maslinski et al., 1992). Although both Jak-1 and p56$^{lck}$ are bound to the non-activated IL-2Rβ chain, the observation that p56$^{lck}$ also binds to the $A^-$ region (Minami et al., 1993) prompted us to examine its role in the dissociation of Raf-1/14-3-3 proteins from the IL-2Rβ chain. In order to perform this examination, COS cells were transfected with IL-2Rβ chain alone, or co-transfected with lck or fyn, then lysed with anti-IL-2Rβ chain antibody. The immunoprecipitates were then probed for the presence of Raf-1 and 14-3-3 proteins by immunoblotting (all procedures as detailed hereinabove).

The results of this examination are shown in FIG. 10a which is a reproduction of the above immunoblot. From these results it is apparent that co-transfection of COS cells with the IL-2Rβ chain and p56$^{lck}$ resulted in the abrogation of Raf-1/14-3-3 binding to the IL-2Rb chain. In contrast, another src-like kinase, p59$^{fyn}$ did not cause this dissociation. In addition, a study of the dissociation of pre-formed IL-2Rβ chain/Raf-1/14-3-3 complexes by enzymatically active p56$^{lck}$ was also carried out. Pre-formed IL-2Rβ chain/(His)$_6$ Raf-1/bacterial 14-3-3 complexes were prepared (see above in respect of FIGS. a–c), exposed to catalytically active p56$^{lck}$ (Upstate Biotechnology), washed and eluted with FLAG peptide. Eluates were separated on SDS-PAGE and tested for the presence of Raf-1 proteins. The results of this study are shown in FIG. 10b which is a reproduction of an SDS-PAGE gel in which is depicted the Raf-1 bands. From these results it is apparent that dissociation of preformed IL-2Rβ chain/Raf-1/14-3-3 complexes by enzymatically active p56$^{lck}$ could also be seen in vitro. It was therefore concluded that activation of p56$^{lck}$ contributes to the dissociation of Raf-1/14-3-3 proteins from the IL-2Rβ chain during IL-2 mediated Raf-1 activation. Since there is no indication that p56$^{lck}$ interacts with Ras-like sequence of the IL-2Rβ chain, it seems that binding of Raf-1 and p56$^{lck}$ to distinct subdomains of the same A-region, co-localize kinase and its substrate for fast enzymatic reaction occurring during IL-2R activation.

Taken together, the above results show that Raf-1/14-3-3 complexes directly associate with the IL-2Rβ chain: the A-region of the receptor is required for Raf-1 binding while the C-terminal portion of the molecule interacts with 14-3-3. These results are consistent with (i) the homology between acidic domain of the IL-2Rβ chain and the effector domain of Ras and Rap1A that binds Raf-1 (FIG. 9); and (ii) the existence of pre-formed Raf-1/14-3-3 protein complexes in the cytosol or co-localized to the plasma membrane (see also Fanti et al., 1994). The IL-2Rβ chain may therefore bypass the requirement for Ras activation in the membrane localization of Raf-1 (see Leevers et al., 1994; Stokoe et al., 1994). Two distinct regions of the IL-2Rβ chain involved in the optimal binding of Raf-1 and 14-3-3 proteins (the acidic A and C-terminal regions, respectively) may enable "permissive" Raf-1 binding and activation, i.e., the IL-2Rβ chain mutant lacking A-region may bind some of Raf-1 proteins through the binding to 14-3-3 proteins associated with C-terminal part (14-3-3 binding domain) of the receptor. For example, BAF cells expressing the mutant IL-2Rβ chain lacking the A-region still respond to IL-2 albeit more weakly than those expressing the wild-type molecule (Hatakeyama et al., 1989). Alternatively, Raf-1 activation occurring in the absence of the IL-2Rβ A domain may be achieved via IL-2 induced activation of Ras (see for example, Izquierdo-Pastor et al., 1995).

In view of the results set forth hereinabove in Examples 1–4, it may be concluded that in accordance with the present invention, it has been shown that the IL-2Rβ chain and Raf-1 interact directly and that the IL-2Rβ chain and 14-3-3 proteins also interact directly. Further, Raf-1 and 14-3-3 proteins bind at different sites on the IL-2Rβ chain and form complexes. The portion of the intracellular domain of the IL-2Rβ chain that is required for binding to Raf-1 has now been defined, this being the so-called acidic region encompassing amino acid residues 313–382 of the mature human IL-2Rβ chain (see also Example 6 below and FIGS. 11 and 12). Further, it has now also been shown that the same portion of the IL-2Rβ chain (acidic domain) is needed for activation of the Raf-1 enzymatic activity (the so-called protein kinase activity). Moreover, while the above acidic domain of the IL-2Rβ chain, that is homologous to the Ras effector domain, is critical for Raf-1 binding, it is the C-terminal portion of the receptor which interacts with 14-3-3 proteins. In the presence of enzymatically active p56$^{lck}$ but not p59$^{fyn}$, Raf-1/14-3-3 complexes dissociate from the IL-2Rβ chain, an event directly related to IL-2 mediated activation of IL-2R and subsequent intracellular signalling. Two in vitro binding assays have been developed which are suitable for screening a number of samples for the presence of compounds or substances which have blocking activity, i.e., that are capable of blocking the binding or interaction of the IL-2Rβ chain to Raf-1, and thereby blocking the signaling pathway initiated by IL-2/IL-15 binding to its receptor (see Examples 5 and 6 below). Such compounds or substances would thereby be useful for the treatment of autoimmune diseases in general, transplant rejection and graft-versus-host rejection process in particular, by being able to block the IL-2/IL-15-mediated signaling pathway.

EXAMPLE 5

In Vitro Assays for Testing Compounds Capable of Disrupting the IL-2R Signaling Pathway As set forth in Examples 1-4 above, two in vitro assays have been developed in accordance with the present invention. The first such assay is a cell-free system in which bacterially produced or mammalian cell (COS cells) produced IL-2Rβ chain fusion proteins are interacted with T cell lysates to isolate, identify and characterize compounds, for example, Raf-1 protein, and 14-3-3 proteins capable of binding specifically to the IL-2Rβ chain intracellular domain or portions thereof. The second such assay is the so-called totally cell-free system in which bacterially produced or mammalian cell produced IL-2Rβ chain fusion proteins are interacted with bacterially produced Raf-1 protein ((His)$_6$-Raf-1) and 14-3-3 proteins to isolate, identify and characterize the nature of the binding between the IL-2Rβ chain intracellular domain or portions thereof and the Raf-1 and 14-3-3 proteins. In both of these assays it is possible to determine both qualitatively and quantitatively the extent of binding between the IL-2Rβ chain intracellular domain or portions thereof, and Raf-1 and 14-3-3 proteins. In the cell-free system it is also possible to determine protein kinase reaction which occurs following the binding of Raf-1 and 14-3-3 proteins to a specific region of the intracellular domain of IL-2Rβ (the acidic domain and the acidic and proline-rich C-terminal region). This determination of the protein kinase reaction is an indicator of the initiation of the intracellular signaling process which is apparently initiated by the binding of Raf-1 and/or 14-3-3 to IL-2Rβ. Therefore, the determination of the protein kinase activity in vitro provides a reliable assay means for determining whether or not another compound, for example, peptides, organic compounds, etc., are capable of disrupting the binding between Raf-1 and 14-3-3 proteins and IL2-Rβ and thereby inhibiting the kinase reaction which is essential to the intracellular signaling mediated by IL-2R.

In the totally cell-free system it arises that in order to be able to determine the Raf-1 protein kinase reaction an additional factor(s) is required, this being most likely a protein of the 14-3-3 family. The establishment of this totally cell-free system and its success for measuring the interaction, i.e., binding between Raf-1, 14-3-3 proteins and IL-2Rβ, permits the further development of this system, i.e., use thereof to isolate and identify the additional factor(s) necessary for utilization of the system to determine the protein kinase activity following binding of Raf-1 and 14-3-3 to IL-2Rβ.

In order to screen compounds such as peptides, organic molecules, etc., for their ability to bind to either the IL-2Rβ chain intracellular domain or specific essential regions thereof and thereby cause inhibition of binding of IL-2Rβ to Raf-1 and 14-3-3 it is possible to utilize any of the above in vitro assay systems. In such a screening assay, bacterially produced or mammalian cell (COS cells) produced IL-2Rβ chain intracellular domain (WT) and/or IL-2Rβ chain intracellular domain analogs such as those containing only the acidic domain or containing both the acidic and proline-rich C terminal domains may be employed as the substrate to which will be exposed samples containing the peptides, organic compounds, etc., which are to be screened to isolate those which specifically bind the IL-2Rβ chain. Once such compounds are obtained, they may be further tested in these screening assays for their ability to inhibit Raf-1 and/or 14-3-3 binding and/or the resulting protein kinase reaction. The procedures to be used in these assays are as detailed hereinabove in Examples 1–4.

It should be mentioned that in the above screening assays it is possible to readily develop an ELISA-type assay system by binding of the FLAG antibody to a microtiter plate sequentially followed by bacterially-expressed or mammalian cell-expressed IL-2Rβ chain-FLAG fusion protein and bacterially-expressed or mammalian cell-expressed Raf-1 and 14-3-3 proteins in the presence (or absence=control) of a potential inhibitor to be screened and finally by an antibody to Raf-1 and/or 14-3-3, this antibody being labelled by standard labels, e.g., radioactive, fluorescent labels or coupled to an enzyme which generates a colored product in the presence of its substrate.

EXAMPLE 6

Compounds Capable of Binding to the Acidic Domain of the IL-2Rβ Intracellular Domain That are Able to Inhibit the Binding of Raf-1 and/or 14-3-3 Proteins to the IL-2Rβ Chain As set forth in Examples 1-4 above, the acidic region of the IL-2Rβ chain is the region responsible for direct binding to Raf-1 and the C-terminal region is responsible for direct binding to 14-3-3 proteins. The acidic region encompasses amino acids 313–382 of the mature human IL-2Rβ chain. Raf-1 and 14-3-3 also form complexes and appear to bind IL-2Rβ and to dissociate therefrom in the form of complexes.

The proline-rich C-terminal portion of the IL-2Rβ chain (amino acids 383–525) is not critical for Raf-1 binding, but is critical for 14-3-3 binding; this portion of the IL-2Rβ chain may at most stabilize Raf-1 binding via the binding of 14-3-3 at this region which is complexed to Raf-1. In FIG. 11, there is shown a scheme of the essential portions of the IL-2Rβ intracellular domain (intracytoplasmic region) that are involved in binding to Raf-1 and are thus directly involved in the IL-2R mediated intracellular signaling. In FIG. 12, there is shown, schematically, the amino acid sequence of the human IL-2Rβ chain. In FIG. 12, the extra cytoplasmic domain is in the upper part of the figure (capital letters); the peptide leader region is indicated by lower letters and the transmembrane region is indicated by underlined letters; and the intracytoplasmic domain is shown in the lower part of the figure, in which the acidic region (a.a. 313–382) is indicated by dotted underlined letters within which region (a.a. 345–371) are shown by italic capital letters the amino acid residues involved directly in IL-2Rβ interaction, of which residues those shown by bold capital italic letters are the acidic residues. The serine residues of the serine-rich region in the intracytoplasmic domain are indicated by crossed-out capital S letters.

One such peptide which is likely to be capable of disrupting the binding between Raf-1 and IL-2Rβ and between Raf-1/14-3-3 and IL-2Rβ is a 27 amino acid peptide derived from analysis of deletion mutants (see Examples 1–4 above), being part of the acidic domain and having a sequence corresponding to amino acids 345–371 of the mature IL-2Rβ chain protein (i.e., peptide having amino acid residues corresponding to amino acids 370 to 396 of SEQ ID No:2, see FIG. 12).

Analogs of the above 27 amino acid peptide will be made by standard chemical synthesis procedures well known in the art or by standard recombinant DNA techniques. Such analogs will include those having one or more amino acids deleted, added or replaced with respect to above 27 amino acid peptide and which will be characterized by their ability to inhibit the binding between Raf-1 and/or 14-3-3 proteins and IL-2Rβ.

Other proteins or peptides which are likely to be capable of specifically binding to Raf-1 and/or IL-2Rβ and which may be capable of inhibiting the binding between Raf-1 and/or 14-3-3 proteins and IL-2Rβ include one or more proteins derived from the 14-3-3 family of proteins or specific peptides derived therefrom or any analogs, derivatives thereof.

As mentioned in Example 4 above, other proteins, peptides, organic compounds, etc., which are capable of binding specifically to Raf-1 and/or 14-3-3 proteins or IL-2Rβ chain intracellular domain and thereby inhibit the binding of Raf-1 and/or 14-3-3 proteins to IL-2Rβ, may be readily obtained by utilization of the in vitro screening assays.

It should be mentioned that of the compounds of potential Raf-1/IL-2Rβ or Raf-1/14-3-3/IL-2Rβ binding inhibitory capability to be screened, organic compounds with some lipophilic characteristics may be most useful in view of the fact that in practice, such compounds to be used pharmaceutically would have to have the ability to pass through the cell membrane. For instance, peptides can be chemically modified or derivatized to enhance their permeability across the cell membrane and facilitate the transport of such peptides through the membrane and into the cytoplasm. Muranishi et al. (1991) reported derivatizing thyrotropin-releasing hormone with lauric acid to form a lipophilic lauroyl derivative with good penetration characteristics across cell membranes. Zacharia et al. (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, the compounds of the present invention, which are capable of inhibiting the binding of Raf-1 and/or 14-3-3 proteins to the cytoplasmic domain of IL-2Rβ, can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g., myristic acid, palmitic acid. These membranes blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), α-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

Further, screening directed at small peptides, e.g., that noted above (having between 20–30 amino acid), is also advantageous to isolate and develop more stable peptidomimetic-type drugs. Once such compounds, peptides, etc., have been screened and found to be capable of binding to Raf-1 and/or 14-3-3 or IL-2Rβ and thereby block the binding between these proteins, these compounds will then be assessed for their expected utility in inhibition of autoimmune diseases in general, and for prevention of transplantation rejection in particular.

The above noted peptides in accordance with the invention may be any peptide of natural origin isolated in the above in vitro screening assays or may be any peptide produced by standard peptide synthesis procedures. Suitable peptides are those capable of interfering with the interaction between Raf-1 and/or 14-3-3 proteins with IL-2Rβ and thereby inhibiting the intracellular signalling process mediated by IL-2Rβ.

Likewise, the above noted organic compounds in accordance with the present invention may be any known pharmaceutically utilized compound or any newly synthetized compound prepared by standard chemical synthesis methods. Suitable such compounds are those capable of interfering with the interaction between Raf-1 and/or 14-3-3 proteins with IL-1 2Rβ and thereby inhibiting the intracellular signalling process mediated by IL-2Rβ.

The above peptides, organic compounds, etc., of the invention may thus be used as the active ingredients in pharmaceutical compositions for the treatment of autoimmune diseases in general, or host-versus-graft reactions in particular. Hence the pharmaceutical compositions of the invention are those comprising a pharmaceutically acceptable carrier, stabilizer or excipient and the above active ingredients of the invention.

The pharmaceutical compositions may be formulated in any acceptable way to meet the needs of the mode of administration. Any accepted mode of administration can be used and determined by those skilled in the art. For example, administration may be by various parenteral routes such as subcutaneous, intravenous, intradermal, intramuscular, intraperitoneal, intranasal, transdermal, or buccal routes. Parenteral administration can be by bolus injection or by gradual perfusion over time.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art.

The total dose required for each treatment may be administered by multiple doses or in a single dose. The pharmaceutical composition of the present invention may be administered alone or in conjunction with other therapeutics directed to the condition, or directed to other symptoms of the condition.

Preparations for parenteral administration include sterile aqueous or non-aqueous solutions, suspensions, and emulsions, which may contain auxiliary agents or excipients which are known in the art, and can be prepared according to routine methods.

Pharmaceutical compositions comprising the inhibitory compounds of the present invention include all compositions wherein the inhibitory compound is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically.

Suitable formulations for parenteral administration include aqueous solutions of the active compounds in water-soluble form, for example, water-soluble salts. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. optionally, the suspension may also contain stabilizers.

Pharmaceutical compositions include suitable solutions for administration by injection, and contain from about 0.01 to 99 percent, preferably from about 20 to 75 percent of active component (i.e., compounds that inhibit the binding of Raf-1 or 14-3-3 proteins to IL-2Rβ) together with the excipient. Compositions which can be administered rectally include suppositories.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Giri et al., *EMBO J.*, 13:2822 (1984).
2. Bamford et al., *PNAS*, 91:4940 (1994).
3. Smith, K. A., *Science*, 240:1169 (1988).
4. Waldmann, T. A., "The IL-2/IL-2 receptor system: A target for rational immune intervention", *Immunol. Today*, 14:264 (1993).
5. Robb, R. J., et al., *J. Exa. Med.*, 160:1126 (1984).
6. Siegal, J. P., et al., *Science*, 238:75 (1987).
7. Hatakeyama, M., et al., "A restricted cytoplasmic region of IL-2 receptor β chain is essential for growth signal transduction but not for ligand binding and internalization", *Cell*, 59:837 (1989).
8. Nakamura, Y., et al., "Heterodimerization of the IL-2 receptor β- and gamma-chain cytoplasmic domains is required for signaling", *Nature*, 369:330 (1994).
9. Noguchi, M., et al., "Interleukin-2 receptor gamma chain: a functional component of the Interleukin-7 receptor", *Science*, 262:1877 (1993).
10. Russell, S. M., et al., "Interleukin-2 receptor gamma chain: a functional component of the Interleukin-4 receptor", *Science*, 262:1880 (1993).
11. Michiel, D. F., et al., "Regulation of the interleukin 2 receptor complex tyrosine kinase activity in vitro", *Cytokine*, 3:428 (1991).
12. Remillard, B., et al., (1991), "Interleukin-2 receptor regulates activation of phosphatidylinositol 3 kinase", *J. Biol. Chem.*, 266:14167.
13. Benedict, S. H., et al., (1987), *J. Immunol.*, 139:1694.
14. Ferris, D. K., et al., (1989), *J. Immunol.*, 143:870.
15. Saltzman, E. M., et al., (1988), *J. Biol. Chem.*, 263:6956.
16. Asao, H., et al., (1990), *J. Exp. Med.*, 171:637.
17. Mills, G. B., et al., (1990), *J. Biol. Chem.*, 265:3561.
18. Merida, I. and G. N. Gaulton, (1990), *J. Biol. Chem.*, 265:3561.
19. Fung, M. R., et al., (1991), "A tyrosine kinase physically associates with the β-subunit of the human IL-2 receptor", *J. Immunol.*, 147:1253.
20. Hatakeyama, M., et al., (1991), *Science*, 252:1523.
21. Turner, B., et al., (1991), "Interleukin-2 induces tyrosine phosphorylation and activation of p72–p74 Raf-1 kinase in a T-cell line", *PNAS (USA)*, 88:1227.
22. Valentine, M. V., et al., (1991), *Eur. J. Immunol.*, 21:913.
23. Carroll, M. P., et al., (1990), *J. Biol. Chem.*, 265:19812.
24. Morrison, D. K., et al., (1988), *PNAS (USA)*, 85:8855.
25. Baccarini, M., et al., (1991), *J. Biol. Chem.*, 266:10941.
26. Kovacina, K. S., et al., (1990), *J. Biol. Chem.*, 265:12115.
27. Blackshear, P. J., et al., (1990), *J. Biol. Chem.*, 265:12131.
28. App, H., et al., (1991), *Mol. Cell Biol.*, 11:913.
29. Heidecker, G., et al., (1992), "The role of raf-1 phosphorylation in signal transduction", *Adv. Cancer Res.*, 58:53.
30. Carroll, M. P., et al., (1991), *J. Biol. Chem.*, 266:14964.
31. D'Andrea, A. D., et al., (1989), *Cell*, 58:1023.
32. Zmuidzinas, A., et al., (1991), "Interleukin-2 triggered Raf-1 expression, phosphorylation, and associated kinase activity increase through G1 and S in CD3-stimulated primary human T cells", *Mol. Cell Biol.*, 11:2794.
33. Maslinski, W., B. et al., (1992), "Interleukin-2 (IL-2) induces tyrosine kinase-dependent translocation of active raf-1 from the IL-2 receptor into the cytosol", *J. Biol. Chem.*, 267:15281.

34. Downward, J., et al., (1990), "Stimulation of p21ras upon T-cell activation", *Nature,* 346:719.
35. Williamson, P., et al. (1994), "The membrane proximal segment of the IL-2 receptor β-chain acidic region is essential for IL2-dependent protein tyrosine kinase activation", *Leukemia 8 Suppl.,* 1:S186.
36. Nelson, B. H., et al., (1994), "Cytoplasmic domains of the interleukin-2 receptor β and γ chains mediate the signal for T-cell proliferation", *Nature,* 369:333.
37. Schorle, H., et al., (1991), "Development and function of T cells in mice rendered interleukin-2-deficient by gene targeting", *Nature,* 352:621.
38. Kundig, T. M., et al., (1993), "Immune responses in interleukin-2-deficient mice", *Science,* 262:1059.
39. Noguchi, M., et al., (1993), *Cell,* 73:147.
40. Strom, T. B., et al., (1993), "Interleukin-2 receptor-directed therapies: Antibody- or cytokine-based targeting molecules", *Ann. Rev. Med.,* 44:343.
41. Riedel, D., et al., (1993), "The mitogenic response of T cells to interleukin-2 requires Raf-1", *Eur. J. Immunol.,* 23:3146.
42. Freed, E., et al., (1994), "Binding of 14-3-3 proteins to the protein kinase raf and effects on its activation", *Science,* 265:1713.
43. Irie, K., et al., (1994), "Stimulatory effects of yeast and mammalian 14-3-3 proteins on the Raf protein kinase", *Science,* 265:1716.
44. LeClair, K. P., et al., (1992), *PNAS (USA),* 89:8145–8149.
45. Blanar, M. A. and Rutter, R. J., (1992), *Science,* 256:1014–1018.
46. McGrew, B. R. et al., (1992), *Oncogene,* 7:33–42.
47. Bruder, J. T., et al., (1992), *Genes and Development,* 6:545–556.
48. Stanton, V. P., et al., (1989), *Mol. Cell Biol.,* 9:639–647.
49. Murakami, M. et al., (1991), *PNAS (USA),* 88:11349–11353.
50. Tsudo M. et al., (1989), *PNAS (USA),* 86:1982–1986.
51. Zhang X. et al., (1993), *Nature,* 364:308–313.
52. Nassar N. et al., (1995), *Nature,* 375:554–560.
53. Miyazaki T. et al., (1994), *Science,* 266:1045–1047.
54. Johnston, J. A. et al., (1994), *Nature,* 370:151–153.
55. Minami Y. et al., (1995), *Immunity,* 2:89–100.
56. Minami Y. et al., (1993), *EMBO J.,* 12:759–768.
57. Fanti, W. J. et al., (1994), *Nature,* 371:612–614.
58. Leevers, S. J. et al., (1994), *Nature,* 369:411–414.
59. Stokoe D. et al., (1994), *Science,* 264:1463–1467.
60. Izquierdo-Pastor et al., (1995), *Immunoloqy Today,* 16:159–164.
61. Moore, B. E. and Perez, V. J., (1967), In: *Physiological and Biochemical Aspects of Nervous Integration,* F. D. Carlson, Eds., Prentice-Hall, Englewood Cliffs, N.J.
64. Aitken, A. et al., (1992), *Trends Biochem. Sci.* 17:498.
63. Fu, H. et al., (1994), *Science* 266:126–129.
64. Reuther, G. W. et al., (1994), *Science* 266:129.
65. Pallas, D. C. et al., (1994), *Science* 265:535.
66. Morrison, D., (1994), *Science* 266:56–57.
67. Muranishi, S. et al., (1991), *Pharm. Research* 8:649.
68. Zaccharia, S. et al. (1991), *Eur. J. Pharmacol.* 203:353–357.

---

What is claimed is:

1. A compound capable of disrupting the binding of Raf-1 protein and 14-3-3 to IL-2Rβ and selected from the group consisting of a peptide having the amino acid sequence corresponding to residues 370 to 396 of SEQ ID NO:2, an analog of said peptide where one amino acid residue of residues 370 to 396 of SEQ ID NO:2 is replaced with a different amino acid residue or deleted, and a chemical derivative of said peptide which enhances the peptide's permeability across the cell membrane or facilitates the transport of the Peptide through the membrane into the cytoplasm, wherein said compound is not a full length human IL-2Rβ chain.

2. A composition comprising:

a compound according to claim 1 or a mixture of two or more different compounds according to claim 1; and a pharmaceutically acceptable carrier, excipient or diluent.

* * * * *